United States Patent [19]

Tanimoto et al.

[11] Patent Number: 4,468,120
[45] Date of Patent: Aug. 28, 1984

[54] FOREIGN SUBSTANCE INSPECTING APPARATUS

[75] Inventors: Akikazu Tanimoto, Kawasaki; Kazunori Imamura, Tokyo, both of Japan

[73] Assignee: Nippon Kogaku K.K., Tokyo, Japan

[21] Appl. No.: 343,552

[22] Filed: Jan. 28, 1982

[30] Foreign Application Priority Data

Feb. 4, 1981 [JP] Japan .................................. 56-14387
Oct. 9, 1981 [JP] Japan ................................ 56-161440
Oct. 9, 1981 [JP] Japan ................................ 56-161441

[51] Int. Cl.³ .......................................... G01N 21/00
[52] U.S. Cl. .................................. 356/237; 250/563; 250/572; 356/239
[58] Field of Search ...................... 356/237, 239, 240; 250/562, 563, 572

[56] References Cited

U.S. PATENT DOCUMENTS 3,814,946  6/1974  Takahashi et al. .................. 250/572
3,879,131  4/1975  Cuthbert et al. ................ 356/237 X
3,984,189 10/1976  Seki et al. ....................... 356/237 X

FOREIGN PATENT DOCUMENTS 128682 10/1979  Japan .................................. 250/562
697892 11/1979  U.S.S.R. ............................. 356/239

Primary Examiner—William L. Sikes
Assistant Examiner—Matthew W. Koren
Attorney, Agent, or Firm—Shapiro and Shapiro

[57] ABSTRACT

An apparatus for detecting the presence of a foreign substance adhering to a planar substrate comprises irradiating means capable of emitting a light beam incident on one surface of the substrate obliquely relative to the surface, means for displacing the irradiating means and the substrate relative to each other so that the position of incidence of the light beam onto the substrate is scanned on said one surface, metering means capable of receiving a plurality of irregular reflected light beams of the light beam which have been irregularly reflected on said surface toward different directions and producing a plurality of electrical outputs corresponding to the intensity of light of the plurality of irregular reflected light beams, and means for deciding the presence of the foreign substance on the basis of the plurality of electrical outputs.

18 Claims, 30 Drawing Figures

FOREIGN SUBSTANCE INSPECTING APPARATUS

BACKGROUND OF THE INVENTION

1. Field of the Invention

This invention relates to an apparatus for detecting foreign substances such as tiny dust, and more particularly to an apparatus for inspecting foreign substances adhering to a substrate such as a photomask, or reticle for LSI.

2. Description of the Prior Art

In the process of manufacturing photomasks or wafers for LSI, foreign substances may adhere to a reticle or a mask and these foreign substances may cause a drawback of the manufactured mask or wafer. In the pattern printing apparatus of the type wherein the pattern on a reticle or the pattern on a mask is reduction-projected onto a mask or a wafer, a plurality of identical chips are formed on the surface of a mask or a wafer. Accordingly, this drawback appears as a drawback common to all of the chips on each mask or wafer and therefore must be strictly inspected in the manufacturing process. Thus, it would generally come to mind to inspect foreign substances with the eye, but this method would usually require much time for inspection and fatigue the operator, thus resulting in a reduced inspection rate.

In recent years, various apparatus for automatically detecting only foreign substances adhering to a mask or a reticle by applying a laser beam thereto have been devised. For example, a laser beam is applied perpendicularly to the mask or reticle and the light spot thereof is scanned two-dimensionally. At this time, the scattered light from the pattern edge on the mask or reticle (the edge of a light-intercepting layer such as chromium or the like) is strong in directivity and the scattered light from a foreign substance is created without directivity. There is known an apparatus for effecting photoelectric detection so as to discriminate between these scattered lights and inspecting, from the scanning position of the light spot, to what portions of the mask or reticle foreign substances adhere. With this apparatus, however, the whole surface of the mask or reticle is scanned by the light spot and therefore, in order to detect small foreign substances, it is necessary to reduce the diameter of the light spot and this has led to a problem that the inspection time is correspondingly lengthened.

Further, with this apparatus, it has been impossible to inspect the so-called adherence conditions of foreign substances, such as discriminating whether foreign substances adhere to the light-intercepting layer such as chromium or the like, whether foreign substances adhere to the glass surface (the light-transmitting portion), or whether foreign substances adhering to the light-transmitting portion lie on the laser light incidence side surface or the opposite surface of the object to be inspected.

SUMMARY OF THE INVENTION

It is a primary object of the present invention to provide an inspecting apparatus which can quickly detect any foreign substance adhering to the surface of an object to be inspected having a light-transmitting property.

It is a further object of the present invention to provide an inspecting apparatus which can quickly detect the adherence conditions of the foreign substance.

It is still a further object of the present invention to provide an inspecting apparatus which can reliably detect any foreign substance on the surface of an object to be inspected having a predetermined pattern formed on the surface thereof.

To achieve these objects, the apparatus according to an embodiment of the present invention is constructed as follows.

A light beam, for example, a laser light, is caused to be incident on the surface of an object to be inspected, and the irradiated portion of the surface is scanned (two-dimensionally) by the light beam. A plurality of light-receiving devices are disposed so that at least one of them does not receive the scattered light created by the pattern and that all of them receive the scattered light created by the foreign substance on the surface, and the presence or absence of the foreign substance is inspected on the basis of the output signals of the light-receiving devices.

The apparatus according to another embodiment of the present invention for achieving the above objects is of the following construction. In an apparatus wherein one surface of an object to be inspected having a light-transmitting property is scanned by a light beam and the presence or absence of a foreign substance adhering to the object to be inspected is inspected on the basis of the light information created from the object to be inspected, there are provided first photoelectric means disposed so as to look to said one surface and to receive the scattered light emitted to said one surface side, second photoelectric means disposed so as to look to the other surface from which the light beam passed through the object to be inspected emerges and to receive the scattered light emitted to said other surface side, and a detecting device for comparing the photoelectric signals of said first and second photoelectric means and producing a detection signal corresponding to the adherence conditions of the foreign substance.

The invention will become more fully apparent from the following detailed description thereof taken in conjunction with the accompanying drawings.

DESCRIPTION OF THE PREFERRED EMBODIMENTS

Figure 1:
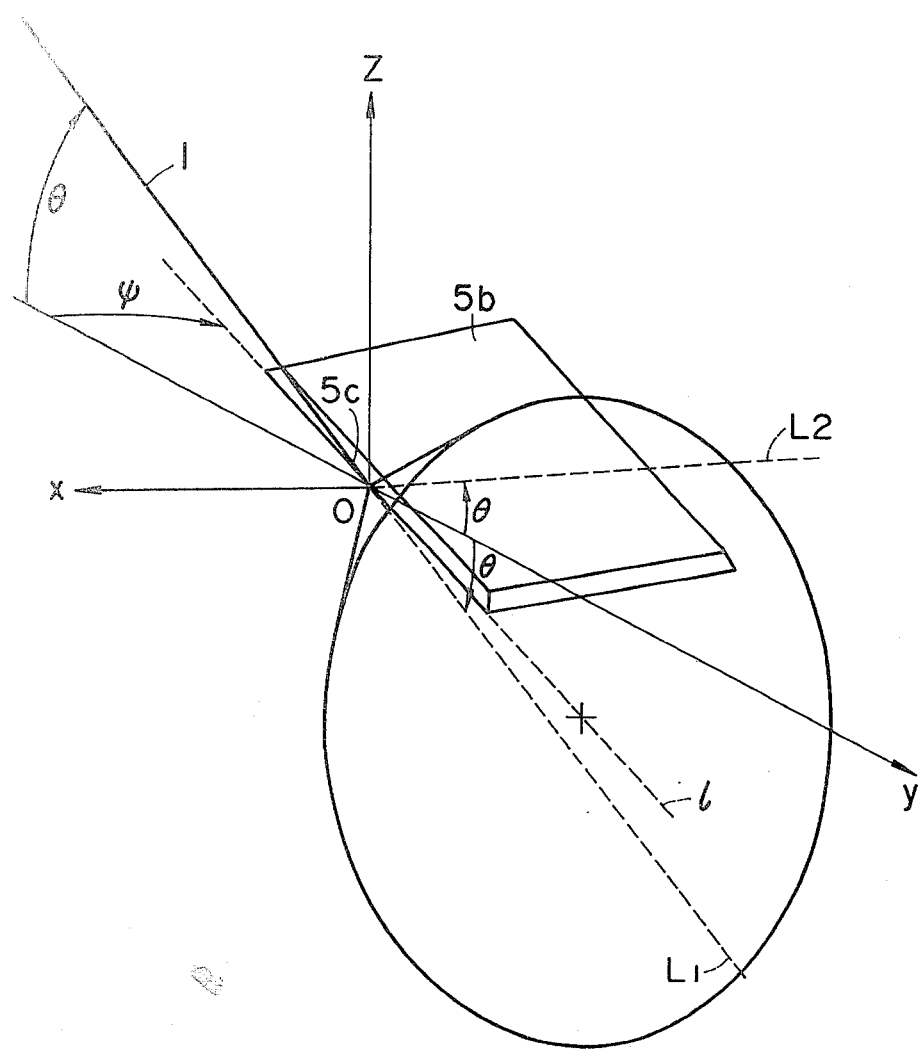
FIG. 1 is a principle diagram illustrating the state of scattered light created when a light beam is applied to the edge of a pattern.

FIG. 1 shows the state of scattering at the edge portion of a circuit pattern when a condensed and stopped down light beam, for example, a laser light, is applied to said edge portion.

In FIG. 1, it is to be understood that the surface to be inspected of a photomask such as a mask or a reticle spreads over the x-y plane of a rectangular coordinates system xyz. A circuit pattern including a light-intercepting layer 5b is provided on the surface to be inspected. It is to be understood that the edge 5c of the light-intercepting layer 5b forms an angle $\psi$ with the y axis. As shown, a laser light 1 is incident on the origin O of the coordinates system xyz. Accordingly, the origin O is the point of incidence. This laser light 1 forms an angle $\theta$ with respect to the surface to be inspected, namely, the x-y plane, and the projection thereof onto the x-y plane is coincident with the y axis. At this time, the scattered light of the laser light 1 is distributed and spreads in a conical shape with the origin O as the vertex on the opposite side from the direction of incidence. This conically shaped scattered light occurs so that it is bisected by the x-y plane.

Where the laser light 1 is obliquely incident on the edge 5c (obliquely incident on the surface to be inspected), the manner of spreading of the scattered light is primarily determined to some extent. As shown, it becomes such a conically shaped scattered light that the transmitted ray and the regular reflected ray of the laser light 1 are the bus lines L1 and L2, respectively, of a cone and the direction 1 of the edge 5c is the center line of the cone. Accordingly, the bus line L1 lies below the x-y plane and the bus line L2 is defined above the x-y plane. Here, as a special case, a case where the angle $\psi$ is 0° and a case where the angle $\psi$ is 90° would come to mind. First, when $\psi = 0°$, the scattered light spreads in a conical shape having a vertical angle $2\theta$ centered about the y axis. When $\psi = 90°$, the vertical angle comes to spread at 180°, namely, on the y-z plane.

Thus, when the laser light is applied to the edge of the pattern, a scattered light having a directional property (strong directivity) due to the angle of incidence onto the edge is created. On the other hand, when a foreign substance is present in the surface to be inspected and laser light is applied thereto, the scattered light spreads in all directions from the foreign substance. Where the foreign substance is sufficiently small as compared with the laser light spot, the laser power per unit area to the foreign substance is invariable and therefore, it is more efficient to make small the angle of incidence $\theta$ on the surface to be inspected and irradiate a wide area of the pattern.

The scattered light so created can be electrically detected by a condenser lens and a photoelectric detector. However, as described above, the scattered light from the edge of the pattern has directivity and therefore, to detect the scattered light from the foreign substance, a plurality of photoelectric detectors may be disposed so as to look to the laser light irradiated portion of the surface to be inspected from different directions.

Figure 2:
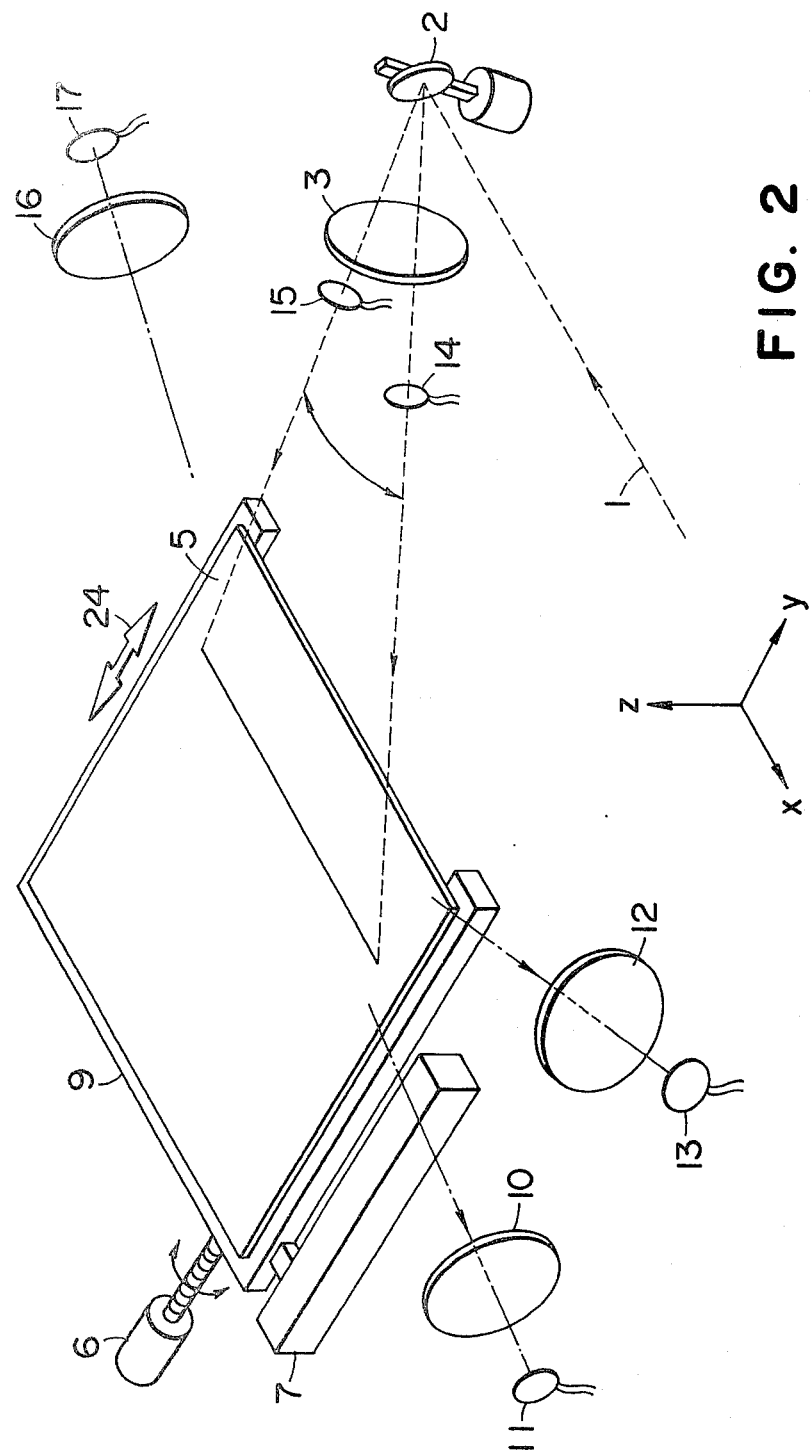
FIG. 2 is a perspective view of the apparatus according to a first embodiment of the present invention.

In a first embodiment of the present invention shown in FIG. 2, it is to be understood that the photomask 5 is a reticle, a mask or a wafer including a circuit pattern. It is also to be understood that the surface of the photomask 5 lies on the x-y plane of the coordinates system xyz. The laser light 1 is suitably converted into any beam diameter by optical members such as an expander (not shown), a condenser lens 3, etc. to increase its intensity of light per unit area. The laser light 1 scans the x direction of the photomask 5 by a scanner 2 such as a vibrator or a galvanomirror. At this time, the scanning laser light 1 is incident obliquely (for example, at an angle of incidence 70°–80°) on the surface of the photomask 5. Accordingly, the shape of the spot on the portion of the photomask 5 irradiated with the laser light 1 is an ellipsoid substantially elongated in the y direction. Also, the scanning position of the laser light 1 scanned by the scanner 2 is detected by photoelectric elements 14 and 15. On the other hand, the photomask 5 is placed on a table 9 and is movable in a direction 24 substantially orthogonal to the scanning direction of the laser light 1 by a moving means 6 such as a motor or the like and scans the irradiated portion in the y direction. A suitable movement amount measuring means such as a linear encoder 7 is provided on the table 9 and the irradiating position of the laser light 1 in the y direction on the photomask 5 can be measured on the basis of the measurement value thereof.

Photoelectric elements 11, 13 and 17 are disposed so as to receive the scattered light from the portion irradiated with the laser light 1 from different directions. The scattered light is condensed on the light-receiving surfaces of the photoelectric elements 11, 13 and 17 by condenser lenses 10, 12 and 16. The optical axes of the respective condenser lenses 10, 12 and 16 are disposed so as to be oblique with respect to the surface of the photomask 5, namely, the x-y plane. This is for the purpose of reducing the influence of the irregular reflection or the like of the pattern surface itself of the photomask 5 by reducing the light-receiving angles, i.e., the angles of the optical axes with respect to the x-y plane. In this embodiment, the photoelectric elements 11, 13 and 17 are disposed substantially equidistantly from the center of the scanning range of the laser light 1.

Description will now be made of the operation of detecting any foreign substance present on the photomask 5 by means of this apparatus. The table 9 is moved in the y direction on the x-y plane while scanning the laser light 1 by the scanner 2. When the laser light 1 irradiates the edge of the pattern during such operation, the scattered light is accompanied by strong directivity as previously mentioned. Thus, of the photoelectric elements 11, 13 and 17 capable of receiving the scattered light from different directions, only a particular photoelectric element receives the scattered light from the edge. Accordingly, the disposition of the photoelectric elements is determined so as not to receive the scattered light from the edge of the pattern simultaneously. Also, when the laser light 1 irradiates the foreign substance during scanning, the scattered light by the foreign substance is created in all directions, namely, almost without directivity. Accordingly, in such case, all of the photoelectric elements 11, 13 and 17 receive the scattered light from the foreign substance. Further where a foreign substance is present near the edge of the pattern, the scattered light from the edge is received by a particular one of the photoelectric elements and the scattered light from the foreign substance is received by all of the photoelectric elements. In this case, the photoelectric output signals of the photoelectric elements assume different values depending on the angle of incidence of the laser light 1 relative to the edge (or to the surface), the size of the foreign substance, etc.

Figure 3:
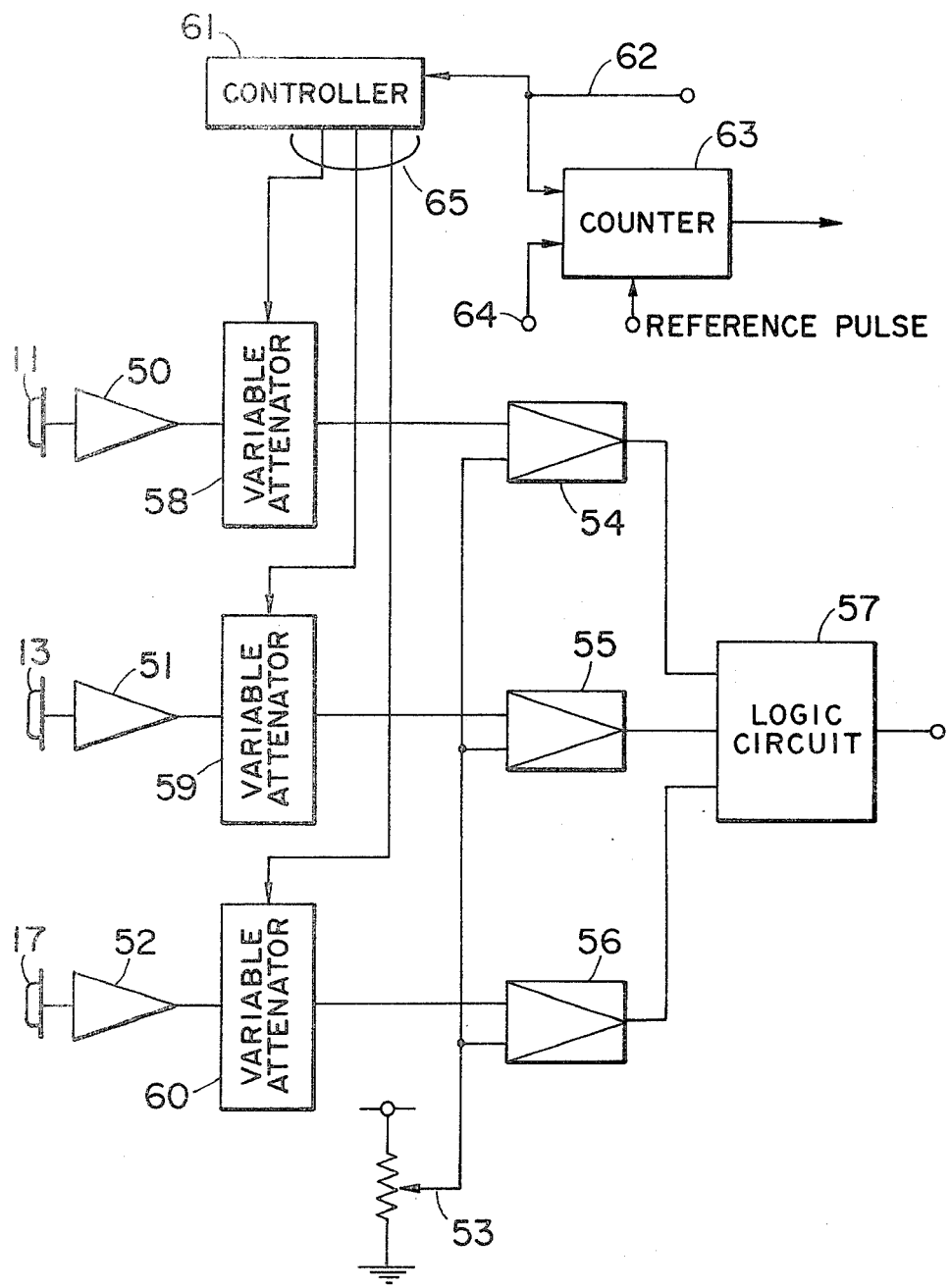
FIG. 3 is a block diagram showing the signal processing system of the apparatus according to the first embodiment.

Therefore, the photoelectric output signal of each photoelectric element 11, 13, 17 is suitably amplified by an amplifier, whereafter the amplified output signal is compared with a reference signal by a comparator, and whether scattered light has been created from the portion irradiated with the laser light 1 toward the photoelectric element is detected. This will be explained by reference to FIG. 3.

The photoelectric signals of the photoelectric elements 11, 13 and 17 are amplified by amplifiers 50, 51 and 52, respectively. The outputs of the amplifiers 50, 51 and 52 have their differences from a reference signal 53 taken by differential amplifiers 54, 55 and 56, respectively.

A logic circuit 57 carries out a predetermined logic operation, for example, a logic product (AND) operation, from the output of each differential amplifier (a digital signal transformed into binary form or an analog signal proportional to the difference). Thus, when each photoelectric element has put out a sufficient photoelectric signal as described above, the logic circuit 57 puts out a predetermined detection signal. That is, it puts out a detection signal only when the laser light 1 is applied to the foreign substance on the photomask 5.

The position of the foreign substance on the photomask 5 is found on the basis of this detection signal, the measurement value by the movement amount measuring means 7 and the scanning position of the laser light 1 by the photoelectric elements 14 and 15.

The photoelectric signals of the photoelectric elements 14 and 15 become greatest when the scanned laser light 1 has crossed each element. Therefore, for example, when the photoelectric signal of the element 14 has become maximum, a counter 63 generates a start signal 62 and starts counting a predetermined reference pulse and, when the photoelectric signal of the element 15 has become maximum, the counter 63 generates a stop signal 64 and stops counting. The pulse number counted during this period is operated by suitable operation means to determine the position of the spot of the laser light 1 on the photomask 5 (the position in the x direction on the x-y plane). The photoelectric signals of the three photoelectric elements 11, 13 and 17 become different in magnitude depending on the position of the spot on the photomask 5. Therefore, when the position of the foreign substance is to be found on the basis of each photoelectric signal, the magnitude of each signal corresponding to the position of the spot is corrected.

For this purpose, amplification degree converters 58, 59 and 60 are provided after the respective amplifiers 50, 51 and 52. Each of these converters comprises, for example, a plurality of resistors, a switch etc. and the resistance value thereof is varied by change-over of the switch. A controller 61 puts out a time-serial sequential signal 65 to the converters 58, 59 and 60 from the point of time whereat the aforementioned start signal 62 is input. This sequential signal 65 is, for example, a signal which generates a pulse at a point of time whereat one scanning period of the laser light 1 is equally divided. The converters 58, 59 and 60 simultaneously effect a time-serial resistance value variation upon application of the sequential signal 65 thereto. By this, the amplification degrees of the amplification degree converters 58, 59 and 60 are varied. At this time, the resistance value variations of the converters 58, 59 and 60 are determined in accordance with the arrangement of the photoelectric elements 11, 13 and 17 relative to the scanning position of the portion irradiated with the laser light 1 and eventually, the variations in amplification degree of the three amplifiers 50, 51 and 52 for time are not identical.

In this manner, by the signal from the foreign substance subjected to a predetermined correction, a signal dependent only on the size of the foreign substance is statistically obtained irrespective of the position of the foreign substance. That is, on the basis of the corrected signal value, said signal may be checked with data regarding the size of the foreign substance statistically obtained in advance.

Figure 4:
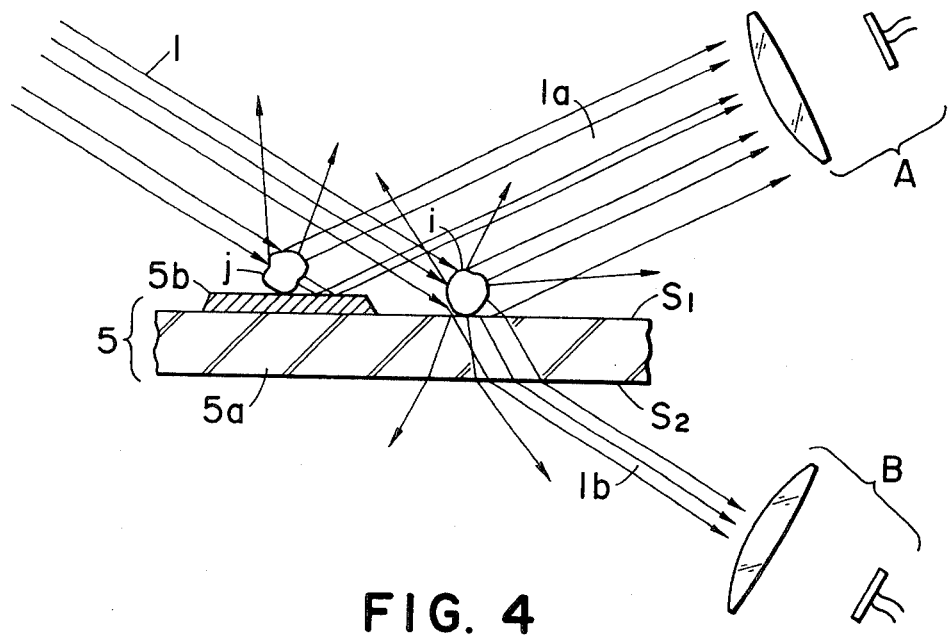
FIG. 4 illustrates the scattering of light by a foreign substance lying on the pattern surface.
Figure 5:
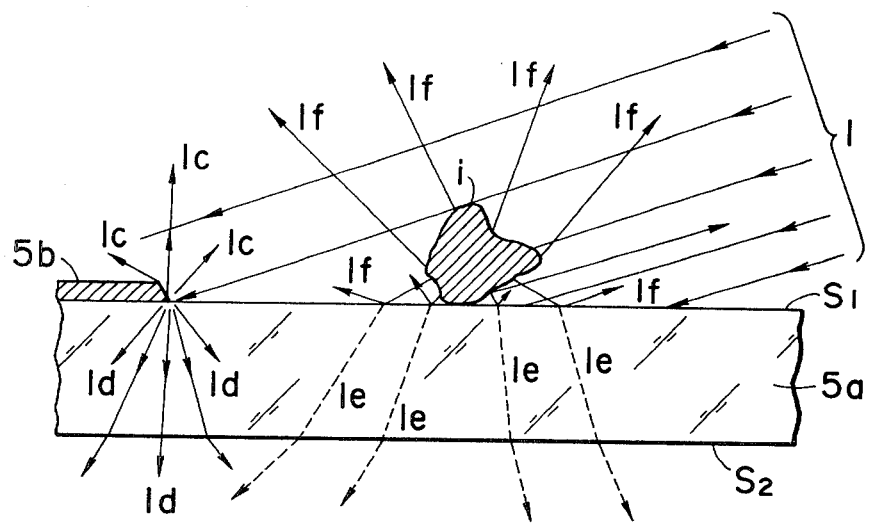
FIG. 5 illustrates the scattering of light by a foreign substance lying on a glass substrate and the scattering of light by the edge portion.
Figure 6:
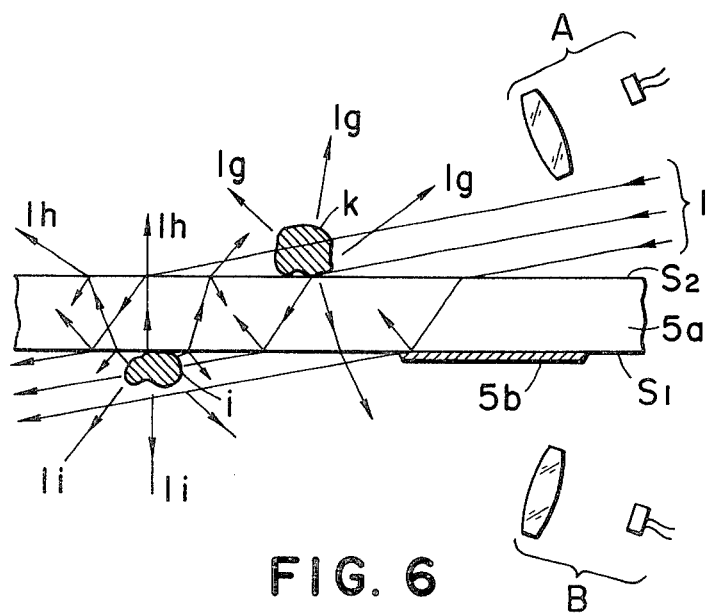
FIG. 6 illustrates the scattering of light by foreign substances lying on the front and back surfaces of the glass substrate.

The relation between the adherence condition of the foreign substance on the object to be inspected and the scattered light will now be considered in greater detail. The states of the scattered light created in accordance with the adherence condition of the foreign substance when a light beam is applied to the object to be inspected are shown in FIGS. 4, 5 and 6. In order to provide good separation of the scattered light from the foreign substance and the scattered light from a light-intercepting layer such as chromium, the light beam is caused to enter the object to be inspected from an oblique direction.

FIG. 4 illustrates the states of the scattering of the laser light by a foreign substance adhering onto the glass substrate of the photomask and the scattering of the laser light by a foreign substance adhering onto the light-intercepting layer when the laser light is applied to a surface of the photomask on which a pattern is depicted. FIG. 5 illustrates the states of the scattering by a foreign substance adhering onto the glass substrate and the scattering by the edge portion of the light-intercepting layer. FIG. 6 illustrates the states of the scattering by foreign substances adhering to the front and back sides of the transparent portion of the glass substrate.

In FIG. 4, the laser light 1 obliquely incident on a pattern surface $S_1$ having a light-intercepting layer $5b$ applied to the glass substrate $5a$ of the photomask 5 is regularly reflected by the glass substrate $5a$ or the light-intercepting layer $5b$. In the figure, the other light beams than the laser light 1 represent only scattered light. A light-receiving portion A comprising a condenser lens and a photoelectric element is depicted as receiving the regular reflected light, but actually it is disposed at such a position that the regular reflected light is not incident thereon. Also, the light-receiving portion A is disposed so as to obliquely look to the portion irradiated with the laser light 1. This is for the purpose of preventing as much as possible the light-receiving portion A from receiving the scattered light created by the fine concavo-concavity of the pattern surface $S_1$ of the glass substrate $5a$ and of the surface of the light-intercepting layer $5b$. Further, a light-receiving portion B including a condenser lens and a photoelectric element is opposed to the surface $S_2$ of the glass substrate $5a$ opposite to the pattern surface $S_1$. This light-receiving portion B is disposed in plane-symmetric relation with the light-receiving portion A with respect to the pattern surface $S_1$ of the glass substrate $5a$, and obliquely looks to the portion irradiated with the laser light 1 from the surface $S_2$ side. The light-receiving portion B is depicted as receiving the laser light directly passed through the glass substrate $5a$, but actually it is disposed at such a position that it does not receive the laser light directly passed through the glass substrate. That is, both the light-receiving portions A and B are disposed at such positions that they receive the scattered light non-directively created from the foreign substance.

Description will now be made of the difference between the scattered light created by the foreign substance i adhering to the transmitting portion of the glass substrate $5a$ and the scattered light created by the foreign substance j adhering onto the light-intercepting layer $5b$.

The magnitude of the photoelectric signal detected by the light-receiving portion A is substantially the same for both of the foreign substances i and j. This is because when the laser light 1 is applied to the foreign substances i and j, the intensity of the scattered light $1a$ non-directively created there is equal if the sizes of the foreign substances i and j are equal. However, the part scattered light $1b$ created by the foreign substance i passes through the glass substrate $5a$ to the light-receiving portion B. Generally, the scattered light $1b$ is smaller than the scattered light $1a$, but some photoelectric signals are produced in the light-receiving portions A and B due to the adherence of the foreign substance i. Of course, the scattered light from the foreign substance j adhering to the light-intercepting layer $5b$ does not reach the light-receiving portion B.

Thus, by examining the photoelectric signals of the light-receiving portions A and B, it is possible to determine whether the foreign substance has adhered to the transparent portion or the light-intercepting layer $5b$ of the glass substrate $5a$.

At the edge portion of the light-intercepting layer $5b$, there are created reflected light of considerably strong directivity and scattered light of non-directivity. Even if the light-receiving portions A and B are so disposed as to receive only the scattered light while avoiding the reflected light of strong directivity from the edge portion, it is necessary to determine whether that scattered light is due to the foreign substance or to the edge portion. This will be explained by reference to FIG. 5. Again in FIG. 5, the light-receiving portions which receive the scattered light are disposed in the same manner as in FIG. 4.

The obliquely incident laser light 1 is mirror-reflected by the pattern surface $S_1$ of the photomask 5 but is scattered at the edge portion of the light-intercepting layer $5b$ by the foreign substance i or the circuit pattern. (Regular reflected light, etc. are not shown.) The light-intercepting layer $5b$, which has a layer thickness of the order of 0.1 $\mu$m, is in intimate contact with the pattern surface $S_1$, so that the scattered light $1c$ travelling directly toward the exterior of the glass substrate $5a$ and the scattered light $1d$ travelling toward the interior of the glass substrate $5a$ are substantially equal in intensity. The scattered light $1d$ passes through the interior of the glass substrate $5a$, whereafter it goes out from the opposite surface $S_2$. On the other hand, the size of the foreign substance is several $\mu$m or larger and, as regards the lights scattered by the foreign substance i, the scattered light $1e$ travelling from the pattern surface $S_1$ toward the interior of the glass substrate $5a$ is weaker than the scattered light $1f$ travelling toward the foreign substance side of the surface $S_1$ because the foreign substance i floats high above the surface $S_1$. This tendency becomes stronger as evident in the difference in magnitude between the photoelectric signals of the light-receiving portions A and B as the angles of elevation in the light-receiving directions of the light-receiving portions A and B relative to the pattern surface $S_1$ are made smaller. This phenomenon can also be explained from the fact that the scattered light behaves as a surface wave to the light-intercepting layer $5b$ which is in intimate contact with the surface $S_1$, while the foreign substance i is in contact with the surface $S_1$ only at a part thereof and most of the foreign substance projects into space and therefore, scattering in free space occurs and when the scattered light is incident at an angle close to the pattern surface $S_1$, the reflection factor becomes high and the rate at which the scattered light enters into the interior from the pattern surface $S_1$ is low. Accordingly, by detecting the scattered light on the pattern surface $S_1$ side by means of the light-receiving portion A and at the same time, detecting the scattered light having passed through the opposite surface $S_2$ by means of the light-receiving portion B, and by determining, for example, whether the ratio of quantity of light between the two scattered lights is twice or greater, it is possible to determine whether the scattering is due to the foreign substance or to the edge portion of the light-intercepting layer $5b$.

Reference is now had to FIG. 6 to describe the principle for discriminating foreign substances adhering to the front and back sides of the glass substrate $5a$. In this figure, the light-receiving portions A and B are obliquely provided rearwardly of the portion of the photomask which is irradiated with the laser light 1, namely, on the incidence side of the laser light 1, and receive the so-called rearward scattered light from foreign substances.

Figure 7A:
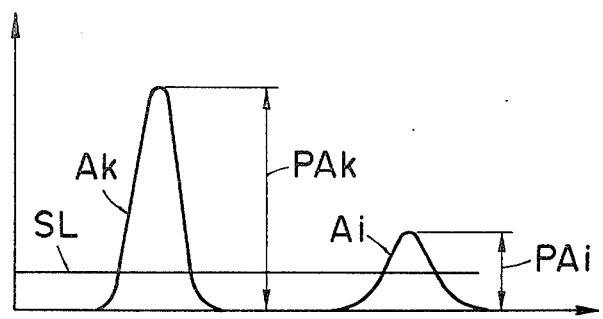
FIG. 7A shows the signal waveform by the light-receiving portion A of FIG. 6.
Figure 7B:
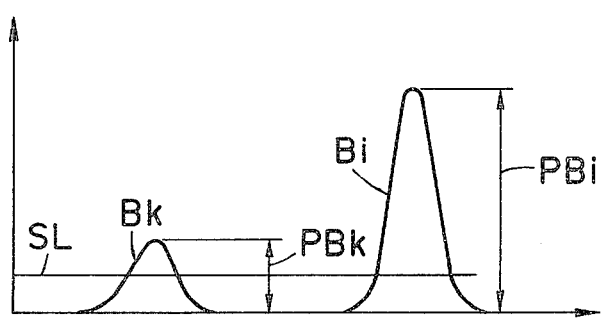
FIG. 7B shows the signal waveform by the light-receiving portion B.

This figure illustrates the difference between the scattering of the laser light 1 by a foreign substance k adhering to the opposite surface $S_2$, namely, the surface of the photomask 5 on which no pattern is formed, and the scattering by a foreign substance i adhering to the surface $S_1$ on which the pattern is formed, when the laser light 1 is incident on the opposite surface $S_2$ of the photomask 5. The laser light 1 is incident on the opposite surface $S_2$ obliquely thereto and part of the laser light is reflected thereby while part of the laser light passes therethrough to the pattern surface $S_1$. The scattered light $1g$ by the foreign substance k is photoelectrically converted by the light-receiving portion A. Of the scattered light by the foreign substance i adhering to the transparent portion of the pattern surface $S_1$, what passes through the interior of the glass substrate $5a$ and appears as scattered light $1h$ on the laser light incidence surface from the opposite surface $S_2$ is photoelectrically converted by the light-receiving portion A. Now, when, of the scattered lights by the foreign substance i, the scattered light $1h$ and the scattered light $1i$ which does not enter the interior of the glass substrate $5a$ from the pattern surface $S_1$ are compared with each other, the scattered light $1h$ is subjected to the reflection loss by the pattern surface $S_1$ and the opposite surface $S_2$ and is therefore weaker in intensity than the scattered light $1i$. The intensity ratio of these two scattered lights tends to become greater as the directions in which the light-receiving portions A and B receive the scattered lights are brought closer to the direction of the opposite surface $S_2$ or the pattern surface $S_1$. This is based on the fact that as the angle of incidence of light is greater, the reflection factor on the surface is increased. Therefore, if the outputs of the light-receiving portions A and B are monitored while varying the position of incidence of the laser light 1 onto the photomask 5, there are obtained signals as shown in FIGS. 7A and 7B. The vertical axes of FIGS. 7A and 7B respectively represent amounts proportional to the intensities of the scattered lights received by the light-receiving portions A and B, and the horizontal axes represent the time or the position of the laser spot relative to the photomask 5. In the scattering of the laser light by the foreign substance k, the light-receiving portions A and B produce signal waveforms Ak and Bk, respectively, and when the magnitudes PAk and PBk of these signals are compared with each other, PAk is three to eight times as great as PBk, and in the scattering by the foreign substance i, there are obtained waveforms such as signal waveforms Ai and Bi and when the magnitudes PAi and PBi of these signals are compared with each other, PBi is three to eight times as great as PAi. Accordingly, when the scattered light exceeds a certain magnitude, if the output ratio of the light-receiving portion A to the light-receiving portion B is K times, for example, two times or greater, it can be judged that the foreign substance adheres to the opposite surface $S_2$ on the laser beam incidence side.

Description will hereinafter be made of the inspecting apparatus of the present invention based on the above-described principle.

Figure 8:
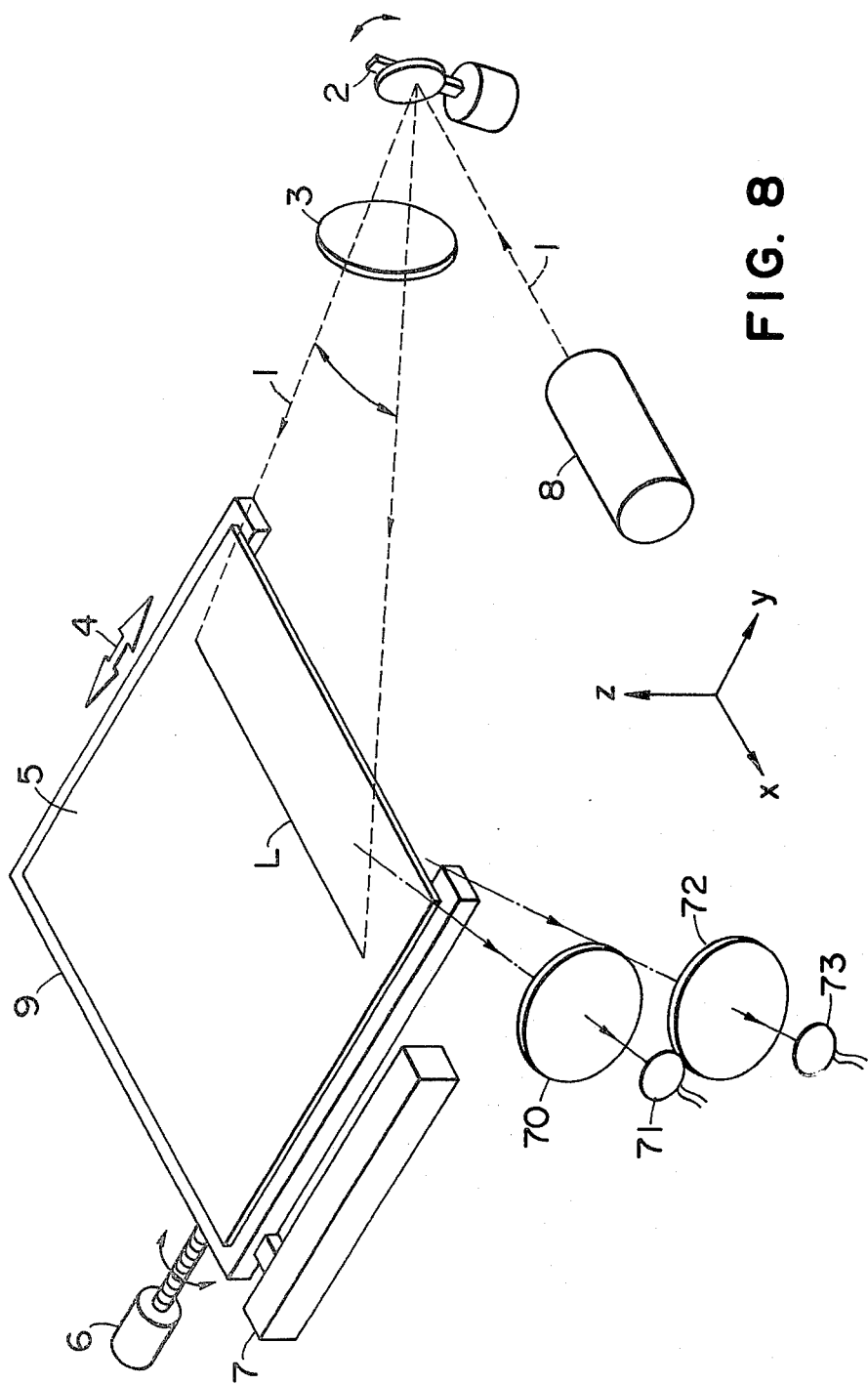
FIG. 8 is a perspective view showing the appearance of the apparatus according to a second embodiment of the present invention.
Figure 9:
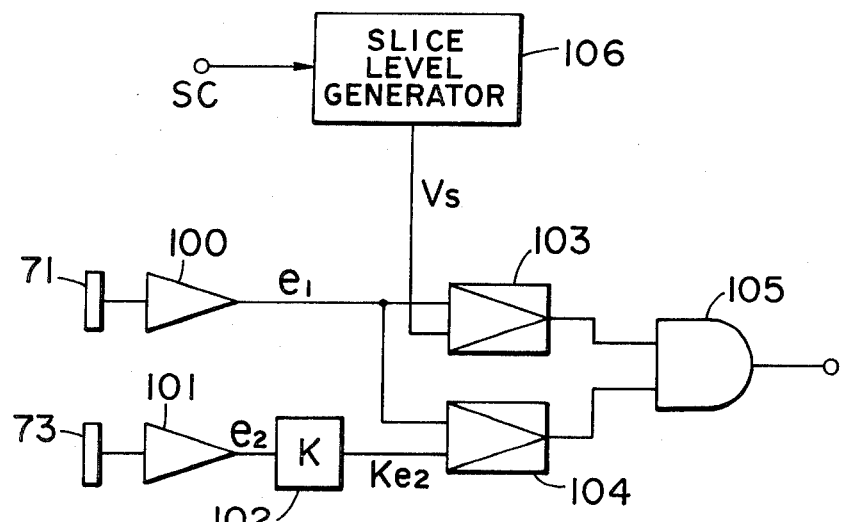
FIG. 9 is a block diagram showing the signal processing system of the apparatus according to the second embodiment.

A second embodiment of the present invention illustrated in FIGS. 8 and 9 is better suited for the inspection of a transparent glass having no pattern thereon or a mask having a relatively simple pattern thereon than for the inspection of a photomask having a complicated pattern thereon.

In FIG. 8, elements common to those of FIG. 2 and designated by identical reference characters need not be described.

There are provided light-receiving elements 71 and 73 for detecting the light information from a foreign substance adhering to the photomask 5, namely, the scattered light created non-directively. Of these light-receiving elements, the element 71 corresponds to the aforedescribed light-receiving portion A and is so disposed as to receive the scattered light created from the front side of the photomask 5 irradiated with the laser light 1. On the other hand, the light-receiving element 73 corresponds to the aforedescribed light-receiving portion B and is so disposed as to receive the scattered light created from the opposite side. Further, the scattered lights are condensed on the light-receiving surfaces of the light-receiving elements 71 and 73 by lenses 70 and 72. The optical axis of the lens 70 is defined so as to look to substantially the central portion of the scanning range L of the laser light 1 from the front side of the photomask 5 so that it is oblique relative to the x-y plane. On the other hand, the optical axis of the lens 72 is defined so as to be plane-symmetric with the optical axis of the lens 70 with respect to the x-y plane. Also, the optical axes of the lenses 70 and 72 are defined so as to be oblique relative to the lengthwise direction of the scanning range L, namely, so as to form a small angle with respect to the x-z plane.

In FIG. 9, the photoelectric signals of the light-receiving elements 71 and 73 are applied as inputs to amplifiers 100 and 101, respectively. The amplified photoelectric signal $e_1$ is applied as input to two comparators 103 and 104. The amplified photoelectric signal $e_2$ is applied to another input of the comparator 104 through an amplifier 102 of amplification degree K. When the quantities of light received by the light-receiving elements 71 and 73 are equal, the signals $e_1$ and $e_2$ are equal in magnitude. The slice voltage Vs from a slice level generator 106 is applied to another input of the comparator 103. The outputs of the comparators 103 and 104 are applied to an AND circuit 105. The slice level generator 106 varies the magnitude of the slice voltage Vs in synchronism with a scanning signal SC for vibrating the scanner 2. This is because, by the scanning of the laser light 1, the distance from the light-receiving element 71 to the irradiation position of the laser light 1 is varied, that is, the solid angle of the lens 70 for the reception of the scattered light is varied. Therefore, design is made such that the slice voltage Vs is variable in synchronism with scanning in accordance with the irradiation position of the laser light 1.

In this construction, the amplification factor K of the amplifier 102 is determined to the range of 1.5–2.5, for example, 2.0. This is because, of the scattered lights created from the substance adhering to the incidence side of the laser light 1, the ratio of the magnitude of the scatted light created on the incidence side to the magnitude of the scattered light passed through the photomask 5 is two times or greater as already described in connection with FIGS. 6, 7A and 7B.

The comparator 103 puts out a logic value "1" only when the signal $e_1$ is greater than the slice voltage Vs.

The comparator 104 compares the signal $e_1$ with $Ke_2$ which is K times as great as the signal $e_2$, and puts out a logic value "1" only when $e_1 > Ke_2$. Accordingly, the AND circuit 105 puts out a logic value "1" only when both the outputs of the comparators 103 and 104 are a logic value "1".

The action and operation of this embodiment will now be described. First, when a foreign substance adheres to the surface on the incidence side of the laser light 1, if the laser light 1 irradiates only that foreign substance, the signal $e_1$ becomes greater than the slice voltage Vs and the comparator 103 puts out a logic value "1". Also, at this time, $e_1 > Ke_1$, and the comparator 104 also puts out a logic value "1". Therefore, the AND circuit 105 generates a logic value "1".

Next, when a foreign substance adheres to the opposite surface, the laser light 1 is obliquely incident on the photomask 5 and therefore, most of the laser light is regularly reflected by the glass surface of the photomask 5 and part of the laser light irradiates the foreign substance on the opposite surface. Therefore, of the scattered lights from the foreign substance, the scattered light reaching the light-receiving element 71 becomes a value smaller than the scattered light reaching the light-receiving element 73, that is, $e_1 < Ke_2$, and the comparator 104 puts out a logic value "0". Therefore, even if $e_1 > Vs$ is established at this time, the AND circuit 105 generates a logic value "0". Where scattered light has been created from the edge portion of the light-intercepting layer, the quantities of light received by the light-receiving elements 71 and 73 become substantially equal, so that $e_1 < Ke_2$ and the comparator 104 puts out a logic value "0". Accordingly, the AND circuit 105 generates a logic value "0".

The magnitude of the slice voltage Vs is related to the foreign substance detecting capability and as the slice voltage Vs is smaller, detection of a smaller foreign substance becomes possible.

Thus, only when a foreign substance adheres to the front side (the laser light incidence side) of the photomask 5, the AND circuit 105 puts out a logic value "1" as the result of the inspection.

As described above, the present embodiment is characterized in that where the scattering by the circuit pattern or the like is so weak that only detection of large foreign substances is required, it can discriminate, by a simple construction, to which of the front and opposite sides the foreign substance adheres and can carry out the inspection at a high speed.

The foregoing description has been made with respect to a case where the laser light is incident from that side on which the circuit pattern is formed and detection of a foreign substance adhering to the incidence surface is carried out. Now, in a reticle or a mask used with a reduction projection exposure device, not only a foreign substance adhering to the circuit pattern side but also a foreign substance adhering to the opposite surface on which no pattern is formed is transferred. If a 1/10 times reduction lens is used, the transferrable minimum size of the foreign substance adhering to the opposite patternless surface is about 1.5 times in length and about two times in area ratio of the transferrable minimum size of the foreign substance adhering to the surface on which the circuit pattern is formed. To detect the foreign substance on the opposite surface, the photomask may be used in its reversed form in the apparatus described in the second embodiment. However, even this will encounter the following problem in the case of a photomask having a complicated pattern thereon. That is, where an attempt is made to determine the size of the foreign substance by the relation between the detected intensity of the scattered light created by the foreign substance on the surface on which no circuit pattern is present and the size of the foreign substance, the relation between the detected intensity of the scattered light by the foreign substance on the circuit pattern surface and the size of the foreign substance becomes different and this leads to an error in the determination of the size of the foreign substance. In addition, detection of the foreign substance becomes difficult under the influence of the scattered light from the edge of the light-intercepting layer of the pattern.

A third embodiment of the present invention will now be described by reference to FIGS. 10–12.

In this third embodiment, in addition to the light-receiving elements 70–73 of the second embodiment, light-receiving systems having substantially equal light-receiving solid angles are provided on that side of the photomask 5 on which the laser light 1 is incident and on the opposite side thereto. Each of these light-receiving systems, as shown in FIG. 10, comprises a condenser lens 80 and a light-receiving element 81 obliquely looking to the front side (the laser light incidence side) of the photomask 5, and a condenser lens 82 and a light-receiving element 83 obliquely looking to the opposite side of the photomask 5. Of course, the optical axes of the lenses 80 and 82 substantially face the central portion of the scanning range L. Further, each of these optical axes is defined so as to coincide with a plane containing the lengthwise direction X of the scanning range L (a plane parallel to the x-z plane of the xyz coordinates system). Also, in this case, the angle formed between the optical axes of the lenses 80 and 70 is determined to the vicinity of 30°–40°. This also holds true of the angle formed between the optical axes of the lenses 82 and 72.

Accordingly, in this embodiment, inspection of a foreign substance is carried out by utilization of the difference in intensity ratio between the lights travelling to the front side and the opposite side of the photomask 5 by the foreign substance and the circuit pattern, in addition to the utilization of the fact that the directivities of the scattered lights by the foreign substance and the circuit pattern differ from each other with respect to the light travelling to the front side of the photomask 5.

FIGS. 11A, 11B, 11C and 11D show variations with time in magnitude of the photoelectric signals from the light-receiving elements 81, 71, 83 and 73, respectively. If the spot of the laser light 1 is scanned at uniform speed on the photomask 5, the horizontal axis also corresponds to the spot position. When the laser light is incident on the circuit pattern and is scattered thereby, the outputs from the photoelectric elements 81, 71, 83 and 73 of FIG. 10 are such as indicated by A1, B1, C1 and D1, respectively, in FIG. 11, and their respective peak values are PA1, PB1, PC1 and PD1. In this case, the scattered light has directivity and therefore, as the photoelectric outputs of the light-receiving elements 81 and 71, the peak PA1 is greater than the peak PB1, but since the directivity is not perfect, the peak PB1 is not zero. The output peak values PC1 and PD1 of the light-receiving elements 83 and 73 on the opposite side of the photomask 5 have values approximate to PA1 and PB1, respectively. This has been described in connection with FIG. 5. However, where the laser light is scattered by a foreign substance, the outputs from the respective light-receiving elements are A2, B2, C2 and D2 and their respective peak values are PA2, PB2, PC2 and PD2. Since the directivity of the scattered light is small, the difference between PA2 and PB2 is small, whereas the differences between PA2 and PC2 and between PB2 and PD2 are great, PA2 and PB2 being greater at the ratio of about three to eight times. Ordinarily, where an attempt is made to slice the signals of FIGS. 11A and 11B with a slice voltage level SL smaller than the smaller peak value PB1, for example, of the scatter signals from the circuit pattern and to detect the weak scattered light by a small foreign substance as much as possible, the circuit pattern will also be judged as a foreign substance. However, if the ratio of the outputs of the light-receiving elements 81 and 83 and the ratio of the outputs of the light-receiving elements 71 and 73 are obtained and if the foreign substance is judged as a foreign substance only when the signal of FIG. 11A exceeds SL and the signal of FIG. 11B also exceeds SL and further when these ratios exceed a predetermined level, for example, two times, then even the use of the above-described low level SL will enable only the foreign substance to be properly detected.

Figure 10:
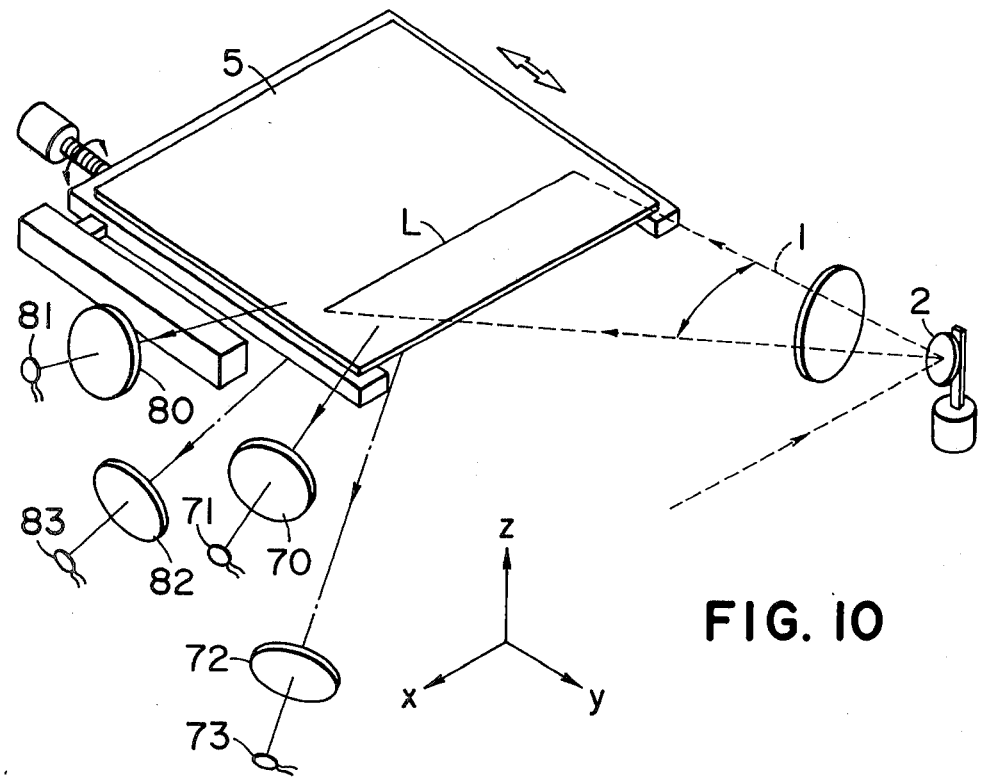
FIG. 10 is a perspective view showing the appearance of the apparatus according to a third embodiment of the present invention.
Figure 12:
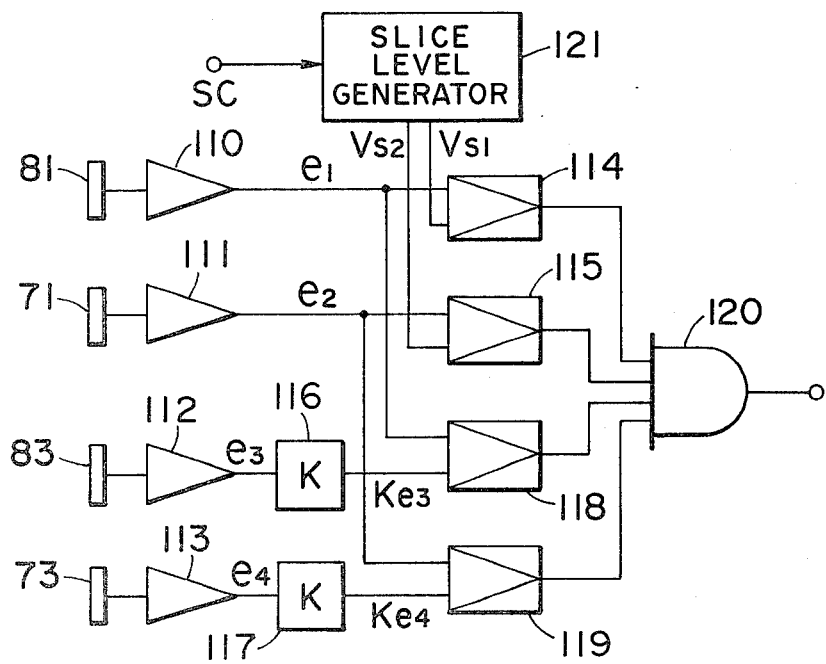
FIG. 12 is a block diagram showing the signal processing system of the apparatus according to the third embodiment.

FIG. 12 is a block diagram of a circuit for the signal processing of the present embodiment, and the outputs of the four light-receiving elements 81, 71, 83 and 73 shown in FIG. 10 are applied as inputs to amplifiers 110, 111, 112 and 113, respectively. These four amplifiers 110–113 are designed such that their output signals $e_1$, $e_2$, $e_3$ and $e_4$ are equal if the quantities of light incident on the four light-receiving elements are equal.

Figure 11A:
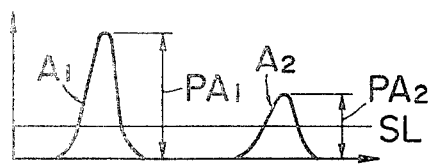
FIGS. 11A–11D are waveform graphs illustrating the outputs of the light-receiving elements in FIG. 10, FIGS. 11A, 11B, 11C and 11D corresponding to the elements 81, 71, 83 and 73, respectively.
Figure 11B:
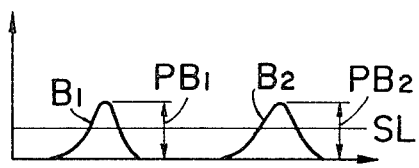
Figure 11C:
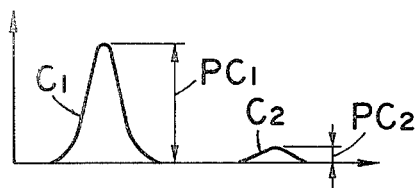
Figure 11D:
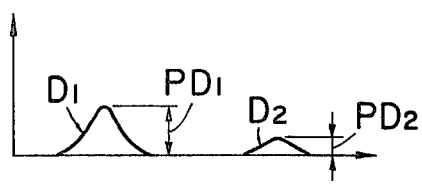

A comparator 114 compares the output signal $e_1$ with a slice voltage $V_{s1}$ as the level SL shown in FIG. 11A, and puts out a logic value "1" when $e_1 > V_{s1}$. A comparator 115 compares the output signal $e_2$ with a slice voltage $V_{s2}$ as the level SL shown in FIG. 11B, and puts out a logic value "1" when $e_2 > V_{s2}$. To discriminate the difference between the scattered lights created on the front and back sides of the photomask 5 by the foreign substance and the edge portion, the output signals $e_3$ and $e_4$ are applied as inputs to amplifiers 116 and 117 of amplification degree K, respectively. This amplification degree K, as in the first embodiment, is determined to a value in the range of 1.5–2.5, for example, 2.0.

A comparator 118 compares the output signal $e_1$ with the output signal $Ke_3$ of the amplifier 116, and puts out a logic value "1" only when $e_1 > Ke_1$. A comparator 119 compares the output signal $e_2$ with the output signal $Ke_4$ of the amplifier 117, and puts out a logic value "1" only when $e_2 > Ke_4$. The outputs of the comparators 114, 115, 118 and 119 are applied as inputs to an AND circuit 120, which, when AND has been established, generates a logic value "1" representative of the fact that a foreign substance is present as a result of the inspection. The slice voltages $V_{s1}$ and $V_{s2}$ are put out from a slice level generator 121 and, as in the first embodiment, their magnitudes vary in response to the scanning signal SC.

Figure 13A:
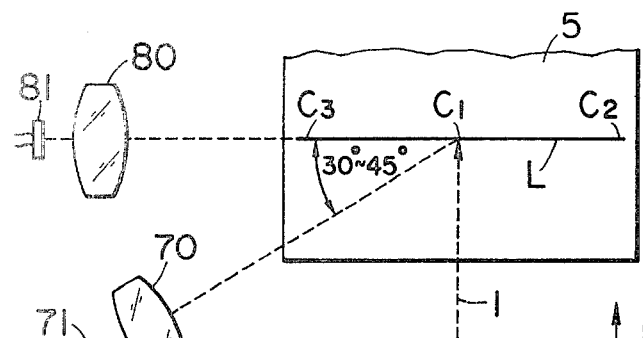
FIG. 13A is a plan view showing a part of the apparatus of FIG. 10.

However, the magnitudes and degrees of variation of the individual slice voltages $V_{s1}$ and $V_{s2}$ differ slightly from each other. This will be described by reference to FIGS. 13A and 13B.

Assume that, in the scanning range L of the laser light 1 on the photomask 5, the central portion thereof is the position $C_1$ and the opposite end portions are the positions $C_2$ and $C_3$, respectively. As previously described, the distances from the light-receiving elements 81 and 71 to the position $C_1$ are equal. Thus, description will hereinafter be made on the assumption that identical foreign substances adhere to the positions $C_1$, $C_2$ and $C_3$. Where a foreign substance adheres to the position $C_1$, the light-receiving solid angles of the light-receiving elements 81 and 71 are substantially equal relative to the scattered light created from that foreign substance and therefore, the magnitudes of the aforementioned signals $e_1$ and $e_2$ are substantially equal. Therefore, when the spot of the laser light 1 lies at the position $C_1$, the slice voltages $V_{s1}$ and $V_{s2}$ are determined to equal magnitudes.

Where a foreign substance adheres to the position $C_2$, the quantity of light received by the light-receiving element 71 is greater than the quantity of light received by the light-receiving element 81. Therefore, the signal $e_2$ is greater than the signal $e_1$ and thus, it is necessary to determine the slice voltage to $V_{s2} > V_{s1}$. However, the difference in magnitude between the signals $e_1$ and $e_2$ is not great since the position $C_2$ is distant from both of the light-receiving elements 81 and 71. Accordingly, the slice voltage satisfies $V_{s2} > V_{s1}$ at magnitudes having not so great a difference therebetween, and is determined to a lever smaller than the slice voltage when at the position $C_1$.

On the other hand, where a foreign substance adheres to the position $C_3$, the signal $e_1$ is of a very great value because the position $C_3$ is closest to the photoelectric element 81. Also, since the light-receiving solid angle of the light-receiving element 71 which looks to the position $C_3$ greatly varies relative to the positions $C_1$ and $C_2$, the signal $e_2$ assumes a smaller value than that at the position $C_1$ or $C_2$. Therefore, the slice voltage satisfies $V_{s1} > V_{s2}$ at a considerably great difference and is determined to a level greater than the slice voltage when at the position $C_1$.

Figure 13B:
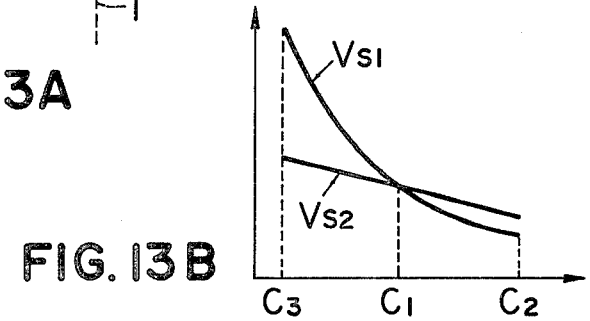
FIG. 13B is a graph showing variations in slice voltages.

The state of variation in each slice voltage relative to the above-described positions $C_1$–$C_3$ is illustrated in FIG. 13B. In FIG. 13B, the vertical axis represents the magnitude of the slice voltage and the horizontal axis represents the position of the scanning range L.

As previously described, the magnitude of the slice voltages $V_{s1}$ and $V_{s2}$ continuously vary so that they become equal at the position $C_1$, that $V_{s2} > V_{s1}$ at the position $C_2$ and that $V_{s1} > V_{s2}$ at the position $C_3$. This variation is not always linear, but is often curved like the variation in the slice voltage $V_{s1}$. To obtain such curved variation, for example, a converter circuit having a logarithmic characteristic or a polygonal line approximation circuit or the like may be used as the slice level generator 121.

Operation of the circuit shown in FIG. 12 will now be described.

Assume that, in contrast with the scattered light created from the edge portion of the pattern, the scattered light has strongly directivity and for example, the quantity of light received by the light-receiving element 71 has become greater than the quantity of light received by the light-receiving element 81. Therefore, the output signals $e_1$ and $e_2$ are in the relation that $e_2 > e_1$. Further, as shown in FIG. 5, the quantities of light received by the light-receiving elements 83 and 73 are substantially equal to the quantities of light received by the light-receiving elements 81 and 71, and the output signals $e_3$ and $e_4$ are in the relation that $e_3 \approx e_1$ and $e_4 \approx e_2$. Therefore, $e_1 < Ke_3$ and $e_2 < Ke_4$, and both of the comparators 118 and 119 put out a logic value "0". Accordingly, the AND circuit 120 generates a logic value "0" for the scattered light from the edge portion.

Also, where scattered light is created from a foreign substance adhering to the pattern surface of the photomask, the output signals $e_1$ and $e_2$ both become greater than the slice voltages $Vs_1$ and $Vs_2$ and the output signals $e_3$ and $3_4$ become $\frac{1}{3}-\frac{1}{8}$ times as great as the output signals $e_1$ and $e_2$. The output signals $e_3$ and $e_4$ become K times as great, but since K is determined to 1.5–2.5, $e_1 > Ke_3$ and $e_2 > Ke_4$. Therefore, all of the comparator circuits 114, 115, 118 and 119 put out a logic value "1" and the AND circuit 120 puts out a logic value "1".

Where scattered light is created from a foreign substances adhering to the opposite surface of the photomask, the quantities of light received by the light-receiving elements 83 and 73 are greater than the quantities of light received by the light-receiving elements 81 and 71, as shown in FIG. 6. Therefore, without fail, $e_1 < Ke_3$ and $e_3 < Ke_4$ and the outputs of the comparators 118 and 119 both become a logic value "0". Accordingly, the AND circuit 120 puts out a logic value "0" for the foreign substance adhering to the opposite surface.

As described above, according to the third embodiment, two pairs of light-receiving elements 71, 73 and 81, 83 are provided so as to selectively intensely receive the scattered light created from the edge portion of the pattern and therefore, even for a photomask having a complicated pattern, only the foreign substance adhering thereto can be accurately detected while avoiding the influence of the scattering by that pattern.

However, in such a detecting circuit, there is a problem that when the scattered light by the pattern is very intense, comparison of the intensities of the scattered lights from the front and back sides of the object to be inspected becomes impossible.

Figure 14:
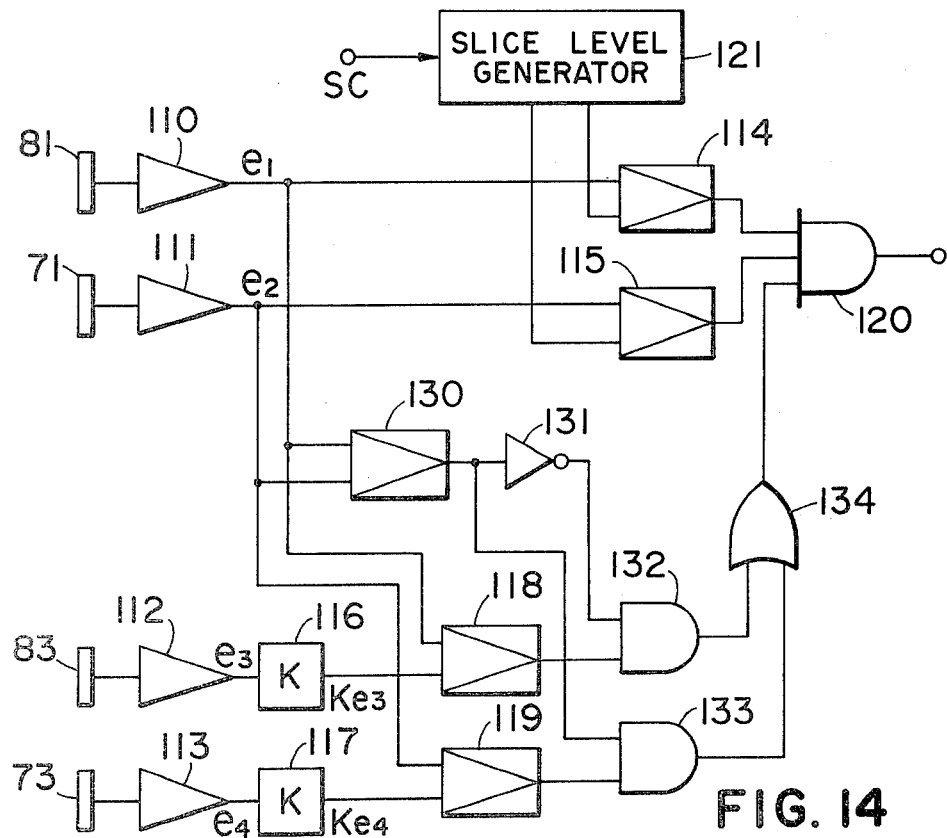
FIG. 14 is a block diagram showing the signal processing system according to a fourth embodiment of the present invention.

Reference is now had to FIG. 14 to describe a fourth embodiment of the present invention in which the construction of the detecting circuit in the third embodiment has been changed to solve such problem. The basic construction of this embodiment is identical to the detecting circuit described in connection with the third embodiment. In this embodiment, however, attention is paid to one of the light-receiving elements 81 and 71 disposed on the laser light incidence side which is smaller in output and design is made such that it is discriminated whether the output ratio is K times or greater between said one light-receiving element and a light-receiving element disposed on the opposite surface side so as to form a pair with said one light-receiving element.

In FIG. 14, elements similar in function or operation to those of FIG. 12 are given similar reference characters. The differences of the construction of FIG. 14 from that of FIG. 12 will hereinafter be described. The output signals $e_1$ and $e_2$ of amplifiers 110 and 111 are applied as inputs to a comparator 130, which detects the magnitudes of the output signals $e_1$ and $e_2$. This comparator 130, for example, puts out a logic value "1" when $e_1 > e_2$, and puts out a logic value "0" when $e_1 < e_2$. The intact output of the comparator 130 and the output thereof inverted by an inverter 131 are connected to one input of AND gates 133 and 132, respectively. The output signals from comparators 118 and 119 are connected to the other inputs of the AND gates 132 and 133, respectively. The output signals of the AND gates 132 and 133 are applied as inputs through an OR gate 134 to an AND gate 120 which generates the result of the inspection.

In such a construction, when, for example, the quantity of light received by the light-receiving element 81 is greater than the quantity of light received by the light-receiving element 71 (due to the scattering by the edge portion or the like of the pattern), the output signals $e_1$ and $e_2$ are in the relation that $e_1 > e_2$. Therefore, the comparator 130 puts out a logic value "1" and the AND gate 132 is closed while the AND gate 133 is opened. Accordingly, if at this time both of the comparators 118 and 119 are putting out a logic value "1", only the output of the comparator 119 is applied to the OR gate 134 through the AND gate 133. Thus, the output of the OR gate 134 represents the result of the discrimination between the foreign substance and the edge portion by the ratio of the photoelectric signals of one of the light-receiving elements 81 and 71 which is smaller in quantity of light received and the light-receiving element which forms a pair with said one light-receiving element (one of the elements 83 and 73).

As described above, selecting the smaller one of the output signals $e_1$ and $e_2$ as in the present embodiment means selecting the light-receiving direction in which the influence of the scattering of the circuit pattern is smaller, and prevents a scattered light of strong directivity from entering into only the light-receiving system in one direction from a fine circuit pattern to cause saturation of the signal processing system, particularly saturation of the output signal of the amplifier, and make impossible the comparison of the intensities of the light-receiving systems on the front and back sides of the object to be inspected and in addition, gives rise to the advantage of reducing erroneous detection of the foreign substance where there is an error in the geometrical arrangement of the condenser lenses of the light-receiving systems looking to the front and back sides of the photomask and the condensing directions on the front and back sides are not completely symmetrical.

In the above-described embodiment, the comparators 118 and 119 seek after $e_1 - Ke_3$ and $e_2 - Ke_4$ for the photoelectric signals as shown in FIGS. 7A and 7B and the outputs thereof are determined depending on whether their results are positive or negative. However, a function similar to that of the above-described embodiment could also be performed by providing a circuit which determines the ratio of $e_1$ and $Ke_3$ and the ratio of $e_2$ and $Ke_4$ by a divider or the like and discriminates whether their results are greater than K.

A fifth embodiment of the present invention will now be described by reference to FIGS. 15 and 16. In this embodiment, one more light-receiving element is added to the third embodiment to further reduce the influence of the scattered light from the pattern.

Figure 15:
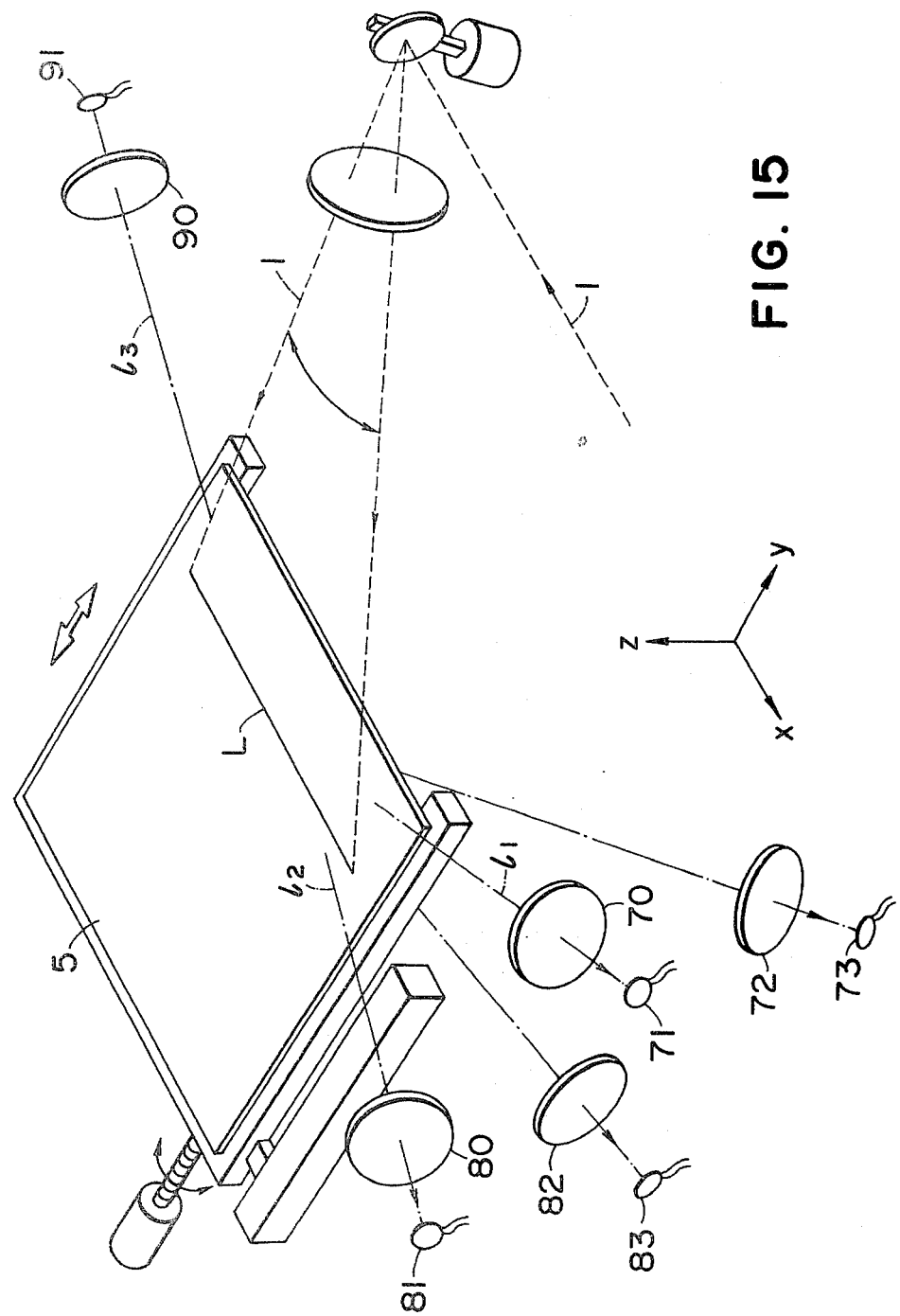
FIG. 15 is a perspective view showing the appearance of the apparatus according to a fifth embodiment of the present invention.

The difference of the construction of FIG. 15 from the construction of FIG. 10 is that a condenser lens 90 and a light-receiving element 91 are so disposed to look to the surface of the photomask 5 on the laser light incidence side, namely, the pattern surface, from the direction opposite to the optical axes of lenses 80 and 70.

The relation between the optical axes of the lenses 70, 80 and 90 will now be described. It is to be understood that these three lenses are of the same optical characteristic and that the characteristics of three light-receiving elements 71, 81 and 91 are also the same. The respective optical axes are designated by $l_1$, $l_2$ and $l_3$. The optical axes $l_1$, $l_2$ and $l_3$ each are determined to a small angle, for example, about 10°–30°, with respect to the pattern surface of the photomask 5. The distances from the central portion of the scanning range L of the laser 1 to the light-receiving elements 71, 81 and 91 are equal. When the photomask 5 is seen from above it in the figure, the optical axis $l_2$ is coincident with the lengthwise direction (scanning direction) of the scanning range L and the optical axes $l_1$ and $l_3$ are determined to a small angle, for example, about 30°, with respect to the scanning range L.

By thus determining the optical axes $l_1$, $l_2$ and $l_3$, the scattered light created by the edge portion of the pattern is hardly received by one of the three light-receiving elements 71, 81 and 91. This has already been described in connection with FIG. 2. The output of the light-receiving element 91 is processed by a detecting circuit shown in FIG. 16. This detecting circuit is basically the same as the detecting circuit of FIG. 14. The output of the light-receiving element 91 is applied as input through an amplifier 140 to a comparator 141. A slice voltage $Vs_3$ corresponding to the spot position of the laser light is applied as input to the comparator 141 from a slice level generator 121 in response to a scanning signal SC. This comparator 141 puts out a logic value "1" when the output signal $e_5$ of the amplifier 140 exceeds the slice voltage $Vs_3$, and puts out a logic value "0" during the other time. The other circuit elements of FIG. 16 are the same as the fourth embodiment. This fifth embodiment, as compared with the fourth embodiment, has a light-receiving system 90, 91 disposed in opposed relationship with the others and is therefore characterized in that the probability with which the scattered light by the circuit pattern is detected as a foreign substance by mistake is very small.

The light-receiving elements 71, 81 and the light-receiving element 91 look to the central portion of the scanning range L from opposite directions and therefore, in contrast with slice voltages $Vs_1$ and $Vs_2$, the tendency of variation of the slice voltage $Vs_3$ becomes reverse. That is, a slice voltage having the reversed tendency of the slice voltage $Vs_2$ in FIG. 13B is the slice voltage $Vs_3$.

Figure 17:
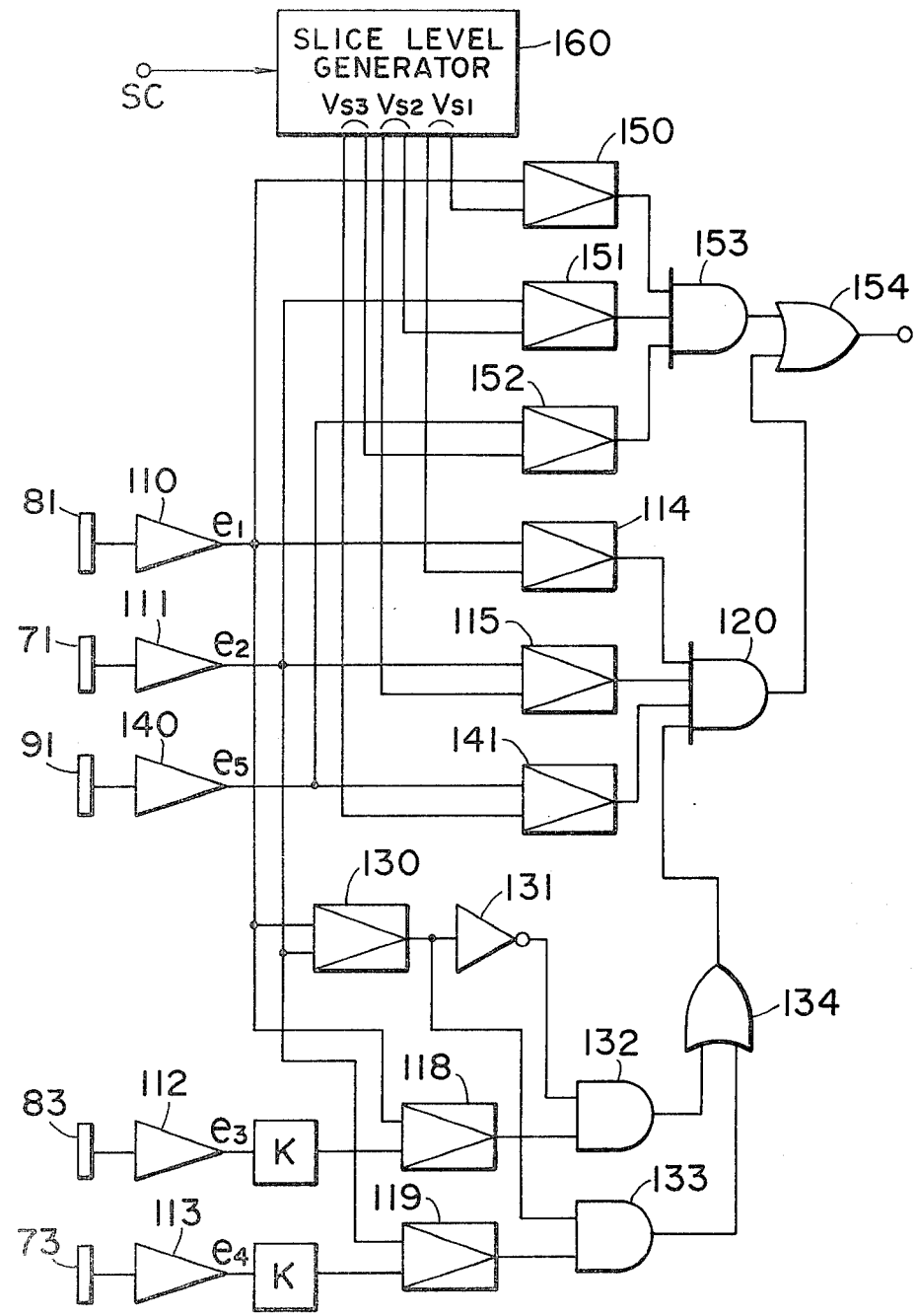
FIG. 17 is a block diagram showing the signal processing system according to a sixth embodiment of the present invention.

FIG. 17 shows a sixth embodiment of the present invention in which the construction of the detecting circuit in the fifth embodiment has been changed. The difference of the sixth embodiment from the fifth embodiment is that three comparators 150, 151, 152, an AND circuit 153, an OR circuit 154 and a slice level generator 160 which generates two types of voltage as the slice voltages $Vs_1$, $Vs_2$ $Vs_3$, respectively, have been added. The two voltages of each slice voltage keep a predetermined difference therebetween and vary in accordance with the scanning signal SC. The output signals $e_1$, $e_2$ and $e_3$ of preamplifiers 110, 111 and 140 are compared with the slice voltages $Vs_1$, $Vs_2$ and $Vs_3$ put out from the slice level generator 160 by the comparators 150, 151 and 152. In this case, the slice voltages applied as inputs to the comparators 150, 151 and 152 are set so that they are higher than the slice voltages applied as inputs to the comparators 114, 115 and 141 and higher than the minimum values of the output signals $e_1$, $e_2$ and $e_3$ however intensely the scattering of light by the circuit pattern may occur. Accordingly, by the comparators 150, 151, 152 and the AND circuit 153, the AND circuit 153 generates a logic value "1" only when a very intense scattered light is created from a foreign substance. The output of the AND circuit 153, with the output of the AND circuit 120, is applied as input to the OR circuit 154. Therefore, irrespective of the size of the foreign substance as the result of the inspection, the OR circuit 154 puts out a logic value "1" when the foreign substance has been detected. This sixth embodiment, as compared with the previous embodiments, has the following feature. Where a great photoelectric signal enters the signal processing system because of the scattering by a foreign substance and the output of each amplifier becomes approximate to the power source voltage, so that the comparators 118 and 119, which compare K times the magnitudes of the outputs of the amplifiers 112 and 113 for the light-receiving elements 83 and 73 disposed on the opposite side of the object to be inspected with the magnitudes of the outputs from the amplifiers 110 and 111, do not accurately operate but both of the comparators 118 and 119 operate as if they detected the scattered light from the circuit pattern in spite of the fact that the scattered light is from the foreign substance, detection of the foreign substance is impossible in the other embodiments, whereas detection of the foreign substance is possible in the present embodiment. This is because, in addition to the comparators 114, 115 and 141 which carry out the comparison with the low slice voltage, there are provided comparators 150, 151 and 152 which carry out the comparison with the high slice voltage and any foreign substance which creates intense scattered light is detected by these comparators.

Detecting a foreign substance by the use of the low slice voltage as in this embodiment contributes to enhanced foreign substance detecting capability, namely, detection of smaller foreign substances while, on the other hand, the use of the high slice voltage contributes to prevention of the erroneous detection by the saturation of amplifiers. This leads to the possibility of detecting the weak scattered light from a smaller foreign substance as well as to the possibility of accurately detecting a foreign substance alone even for intense scattered light. This means an enlarged foreign substance detection range.

The detecting circuit according to the sixth embodiment has been described with respect to an example in which three light-receiving elements are disposed on the laser light incidence side of the object to be inspected and two light-receiving elements are disposed on the opposite side, but if there are one or more light-receiving elements on the respective sides as in the previous embodiments, it will of course be possible to design the detecting circuit such that it is endowed with the function intended by the sixth embodiment.

Figure 16:
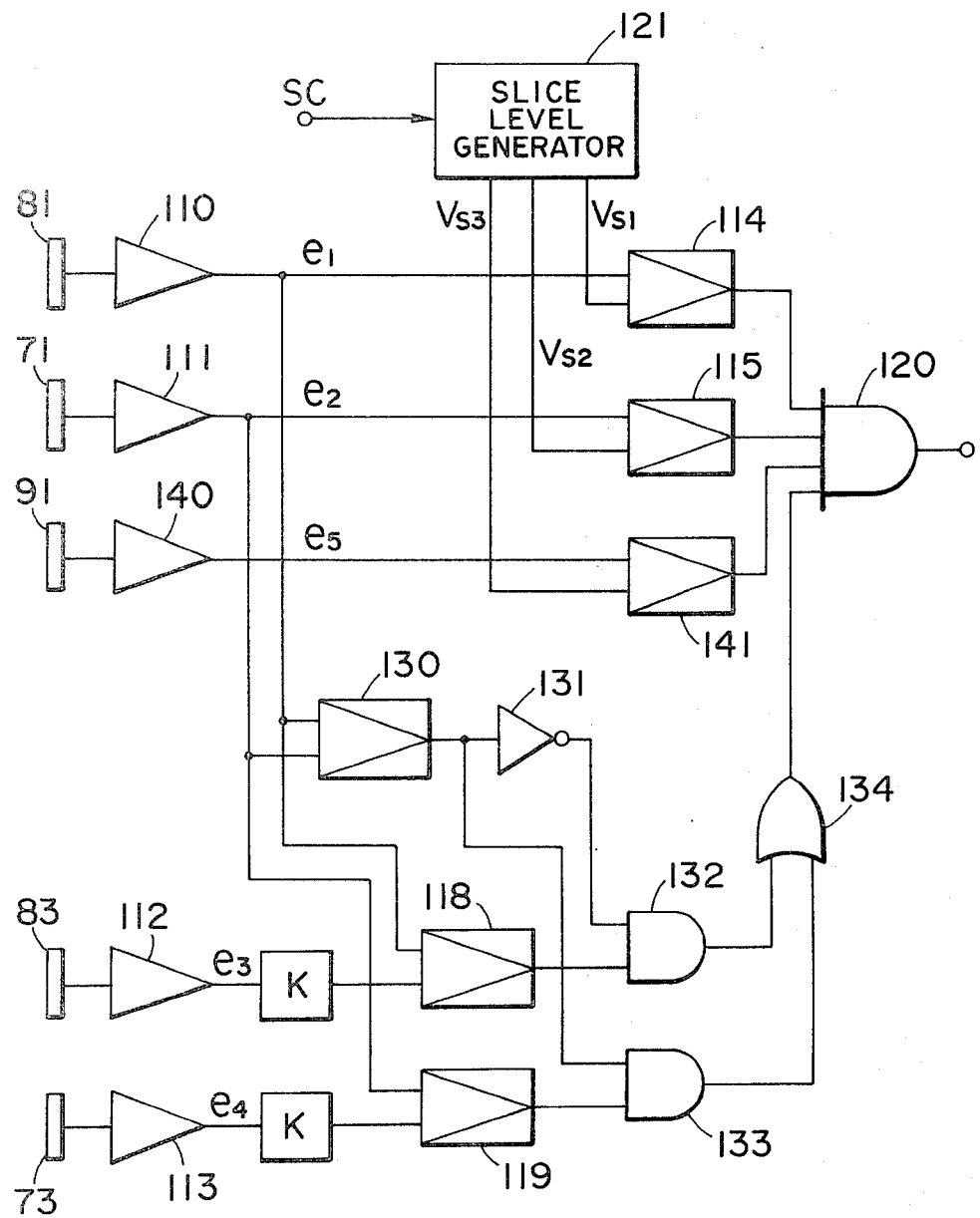
FIG. 16 is a block diagram showing the signal processing system of the apparatus according to the fifth embodiment.

In FIGS. 14, 16 and 17, use is made of comparator 130, AND gates 132, 133 and OR gate 134, but as shown in FIG. 12, the outputs of comparators 118 and 119 may be connected so as to be directly applied to AND circuit 120.

Figure 18:
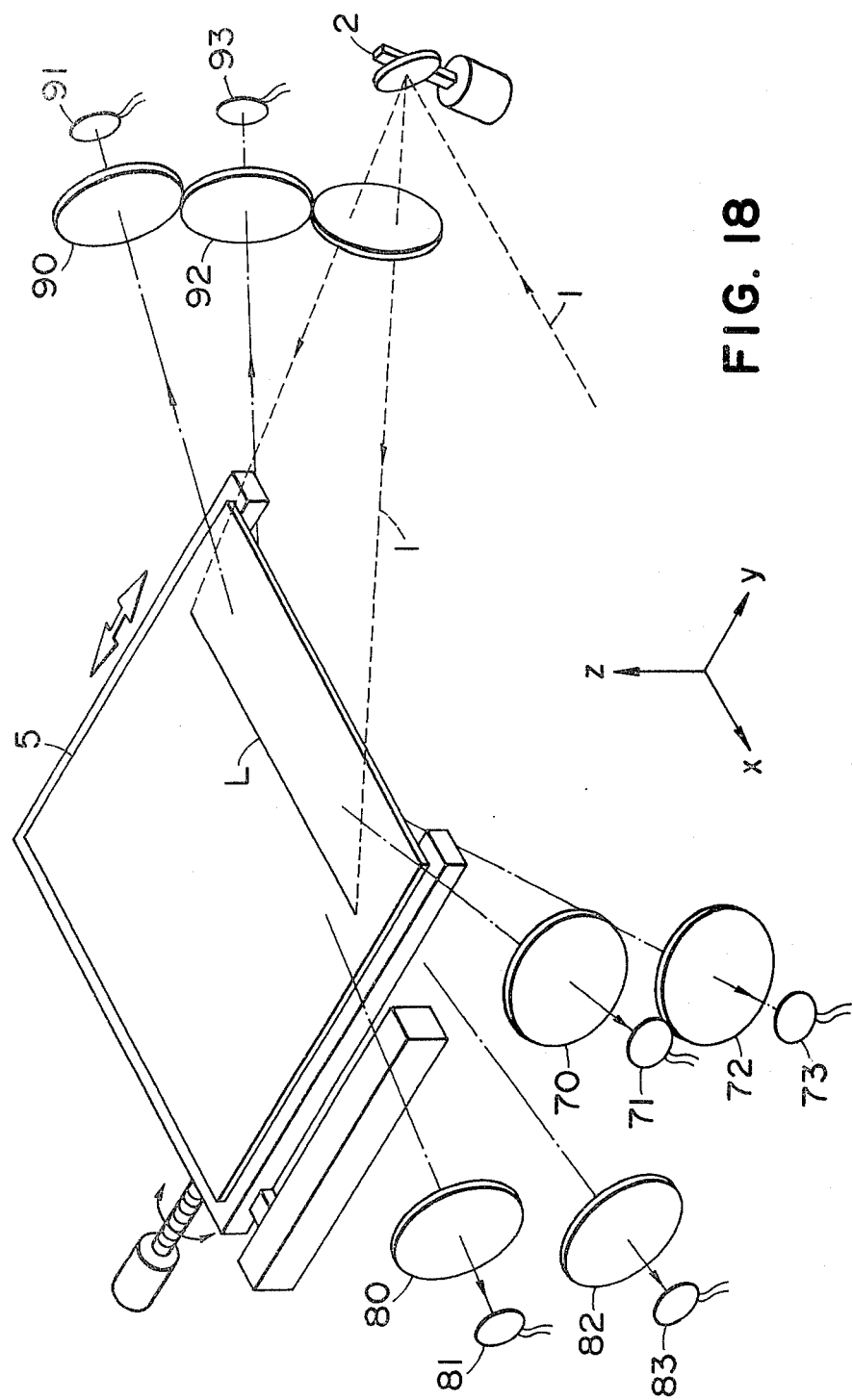
FIG. 18 is a perspective view showing the appearance of the apparatus according to a seventh embodiment of the present invention.

A seventh embodiment of the present invention will now be described by reference to FIG. 18. In this embodiment, one more light-receiving element 93 and condenser lens 92 are added to the sixth embodiment. The optical axis of this lens 92 is determined so as to be plane-symmetric with the optical axis of the lens 90 with respect to the pattern surface of the photomask 5. Of course, the optical axis of the lens 92 is determined so as to look to the central portion of the scanning range L from the opposite surface of the photomask 5. In this embodiment, the photoelectric signals of the light-receiving elements 71, 81 and 91 which receive the scattered light from the laser light incidence side are compared with the slice voltages as in the previous embodiments and processed so as to obtain the AND. By this, it is discriminated whether the scattered light from the edge portion of the pattern is the scattered light from a foreign substance. On the other hand, the photoelectric signals of the light-receiving elements 73 and 83 for processing the scattered light from the opposite surface of the photomask 5 may be processed by a detecting circuit such as that of the previous embodiment, but can be processed by a simpler detecting circuit.

Figure 19:
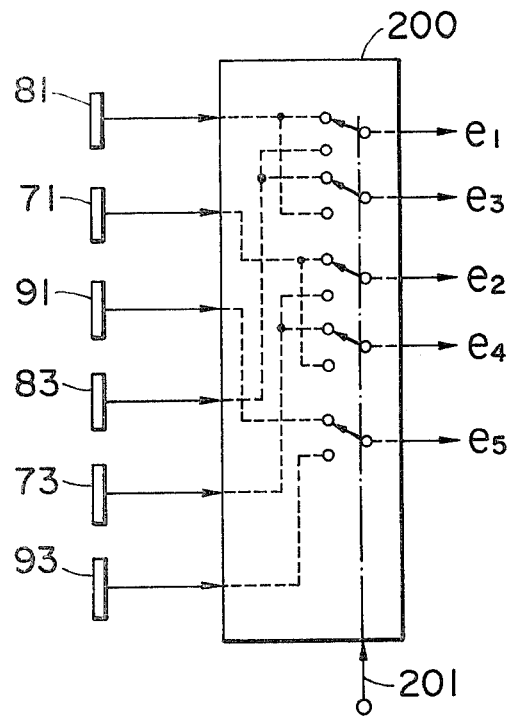
FIG. 19 is a wiring diagram showing a change-over circuit used in the seventh embodiment.

For example, the photoelectric signals of the light-receiving elements 73, 83 and 93 may be processed by a circuit constructed similarly to the detecting circuit of the light-receiving elements 71, 81 and 91. If this is done, when the light-receiving elements 71, 81 and 91 on the laser light incidence side detect a foreign substance and the foreign substance is detected also by the light-receiving elements 73, 83 and 93 on the opposite surface side, that foreign substance can be discriminated as adhering to the transparent portion of the photomask 5. In this case, there is an advantage that the size of the foreign substance can be very accurately found by considering the peak value of the photoelectric signal of each of the light-receiving elements when the foreign substance has been detected both on the front and back sides of the photomask 5.

Where the detecting circuit in the embodiment of FIGS. 5 and 6 is intactly used, a change-over circuit 200 as shown in FIG. 19 may be provided. This change-over circuit 200 is designed to change over the photoelectric signals of the light-receiving elements 71, 81 and 91 on the laser light incidence side and the photoelectric signals of the light-receiving elements 73, 83 and 93 on the opposite side and generate output signals $e_1$–$e_3$. Of course, the point whereat this change-over takes place may be after the photoelectric signal of each light-receiving element has once been amplified. This change-over is effected by a signal 201. With such a construction, when, for example, the opposite surface of the photomask 5 is to be inspected, the operation of reversing the photomask 5 before placing it becomes unnecessary. Therefore, the laser light 1 may be directed to the opposite surface of the photomask 5 in FIG. 17 by a suitable optical path change-over member in the same manner as when the laser light is applied to the front surface of the photomask.

If the signal 201 is changed in response to the change-over of the optical path change-over member, the operation of reversing the photomask 5 is unnecessary and therefore, foreign substances adhering to the both surfaces can be accurately detected within a very short time.

Figure 20A:
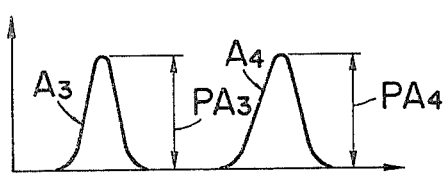
FIGS. 20A–20D are waveform graphs showing the outputs of the light-receiving elements in FIG. 10, FIGS. 20A, 20B, 20C and 20D corresponding to the elements 81, 71, 83 and 73, respectively.
Figure 20B:
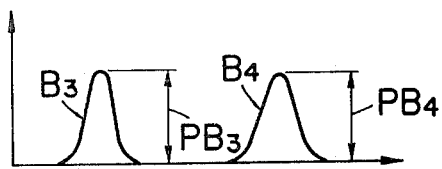
Figure 20C:
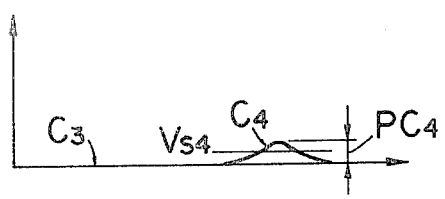
Figure 20D:
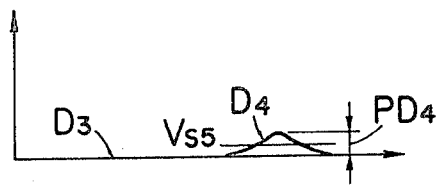

As previously described by reference to FIG. 4, the scattered light from the foreign substance i adhering to the transmitting portion of the glass substrate 5a of the photomask is detected by the light-receiving portions A and B, while the scattered light from the foreign substance j adhering to the light-intercepting layer 5b is detected only by the light-receiving portion A and not by the light-receiving portion B. This will hereinafter be described as the photoelectric signal of each light-receiving element of FIG. 10 by reference to FIG. 20. FIGS. 20A, 20B, 20C and 20D show the photoelectric signals from the light-receiving elements 81, 71, 83 and 73, respectively, with the vertical axis representing the magnitudes of such signals and the horizontal axis representing time. The horizontal axis also corresponds to the laser spot position. When the laser light is scattered by the foreign substance j as shown in FIG. 4, the light-receiving elements 81 and 71 produce photoelectric signals A3 and B3, respectively, as shown in FIGS. 20A and 20B. On the other hand, the light-receiving elements 83 and 73 respectively put out substantially zero as photoelectric signals C3 and D3, as shown in FIGS. 20C and 20D. When the laser light is scattered by the foreign substance i as shown in FIG. 4, the light-receiving elements 81, 71, 83 and 73 produce photoelectric signals A4, B4, C4 and D4, respectively, as shown in FIG. 20. That is, as shown in FIGS. 20C and 20D, the photoelectric signals C4 and D4 of the light-receiving elements 83 and 73 are not zero but some outputs are obtained therefrom. PA4, PB4, PC4 and PD4 are the peak values of the photoelectric signals A4, B4, C4 and D4. Thus, if small slice voltages $V_{s4}$ and $V_{s5}$ are valves intermediate the peak values PC4 and PD4, respectively, in the case of the foreign substance i, the photoelectric signals of the light-receiving elements 83 and 73 both exceed the slice voltages $V_{s4}$ and $V_{s5}$, while in the case of the foreign substance j, they do not exceed the slice voltages $V_{s4}$ and $V_{s5}$ and thus, distinction can be made between the foreign substances i and j. An eighth embodiment will now be described specifically. In this embodiment, light-receiving elements are disposed in the same manner as in FIG. 10.

Figure 21:
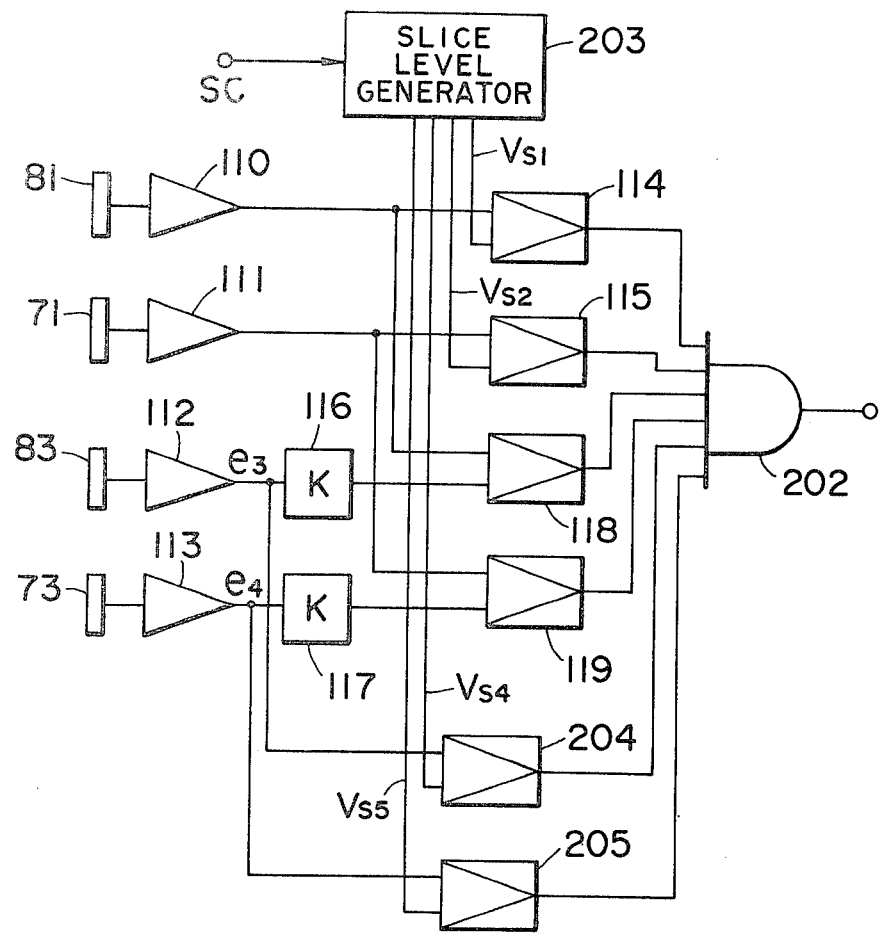
FIG. 21 is a block diagram showing the signal processing system according to an eighth embodiment of the present invention.

FIG. 21 is a block diagram of the signal processing system of the present embodiment. Light-receiving elements 81, 71, 83, 73, amplifiers 110–113, comparators 114, 115, 118, 119 and amplifiers 116, 117 have the same functions as the circuit of FIG. 12. The difference of this embodiment from that of FIG. 12 is that comparators 204 and 205 are provided and their outputs are applied parallel to an AND circuit 202. The comparator 204 compares the output $e_3$ of the amplifier 112 with a slice voltage $V_{s4}$ put out from a slice level generator 203 and puts out a logic value "1" if $e_3 > V_{s4}$, and puts out a logic value "0" if not so, while on the other hand the comparator 205 compares the output $e_4$ of the amplifier 113 with a slice voltage $V_{s5}$ and puts out a logic value "1" if $e_4 > V_{s5}$, and puts out a logic value "0" if not so. The magnitudes of the slice voltages $V_{s4}$ and $V_{s5}$ are determined in the manner as described in connection with FIGS. 13A and 13B and vary correspondingly to the spot position. The manner of variation is such as described in connection with the embodiments of FIGS. 2–7. In such a construction, when the laser light impinges on a foreign substance adhering to the light-transmitting portion of the glass substrate, the comparators 204 and 205 put out a logic value "1" and the other comparators 114, 115, 118 and 119 also put out a logic value "1" and therefore, the output of the AND circuit 202 assumes a logic value "1", thus indicating that the foreign substance has been detected. However, when the laser light is incident on a substance adhering to the light-intercepting layer, the outputs of the comparators 204 and 205 assume a logic value "0" and the output of the AND circuit 202 assumes a logic value "0". Accordingly, only when a foreign substance adheres only to the light-transmitting portion, the presence of the foreign substance can be detected and any foreign substance adhering to the light-intercepting layer which does not affect the printing of the mask pattern may be neglected.

Thus, as compared with a case where detection of a foreign substance is effected without making distinction between the light-transmitting portion and the light-intercepting layer as to the location to which the foreign substance adheres, the present embodiment reduces the necessity of re-cleaning a photomask as a contaminated one in spite of the photomask having a foreign substance adhering only to the light-intercepting layer thereof and the degree of cleanness thereof being sufficiently high to permit printing of the pattern, or the necessity of replacing such photomask with another photomask having the same pattern. This leads to saving of time and economical advantage in the manufacture of semiconductor devices.

In this eighth embodiment, both of the outputs of the comparators 204 and 205 are applied as inputs to the AND circuit 202, but alternatively only one of the outputs of the comparators 204 and 205 may be applied as input to the AND circuit 202. In that case, the construction will become simpler but malfunctioning may occur if noise is mixed with the photoelectric signals. It is also conceivable to obtain the OR of the outputs of the comparators 204 and 205 and apply the result thereof as input to the AND circuit 202.

In the foregoing, this eighth embodiment has been described as an embodiment in which the new function of detecting a foreign substance adhering only to the light-transmitting portion has been added to the third embodiment, but of course, such function can be equally added to the other embodiments.

In each of the above-described embodiments, the light-receiving element for receiving the scattered light created on the laser light incidence side and the light-receiving element for receiving the scattered light created on the opposite side are disposed symmetrically relative to the surface of the object to be inspected.

This is because a photomask is used as the object to be inspected, and for example, in a case where inspection of an object having a pattern of light-intercepting layer depicted on the transparent substrate thereof but having no edge portion is carried out, the pair of light-receiving elements looking to the front and back sides of the substrate need not always be disposed plane-symmetrically. Also, a plurality of light-receiving elements looking to the laser light incidence side surface may be provided and a single light-receiving element looking to the opposite surface may be provided.

Figure 22:
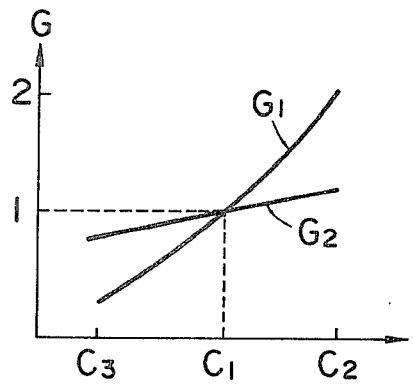
FIG. 22 is a graph illustrating the gains of amplifiers.

In the detecting circuit of each of the above-described embodiments, the slice voltages are varied in accordance with the spot scanning position of the laser light, but where the variation in the scattered light receiving solid angle of each light-receiving element is small relative to the spot scanning position, the slice level may be constant and need not be varied. Also, even where the scattered light receiving solid angle is varied by the laser spot scanning, the slice voltages need not always be varied but may be fixed to predetermined values if the gain of the photoelectric signal transmission system is varied correspondingly to the laser spot scanning position, i.e., in synchronism with the scanning signal SC.

Where the gain of the transmission system is thus controlled, for example, the slice voltages $V_{s1}$ and $V_{s2}$ in FIGS. 12 and 14 are made into a common predetermined voltage. Also, the gains of the amplifiers 110 and 111 are made variable in accordance with the spot position of the laser light 1. As an example, the relation between the gains of the amplifiers 110 and 111 may be determined as shown in FIG. 22. FIG. 22 corresponds to FIG. 13B and at the position $C_1$, the gain $G_1$ of the amplifier 110 and the gain $G_2$ of the amplifier 111 are made equal to each other. The then gain is regularized into 1. For example, at the position $C_2$, the gain $G_1$ may be determined to about two times the gain at the position $C_1$ and the gain $G_2$ may be determined to 1.2–1.5 times the gain at the position $C_1$, and at the position $C_3$, the gain $G_1$ may be determined to 0.2–0.4 times the gain at the position $C_1$ and the gain $G_2$ may be determined to 0.7–0.9 times the gain at the position $C_1$.

In the above-described embodiments, the ratio of the outputs of the pair of light-receiving elements provided correspondingly to the front and back sides of the object to be inspected has been compared with a certain value K, but for example, by obtaining the sum of the outputs of the light-receiving elements 71 and 81 positioned on the front side and the sum of the outputs of the light-receiving elements 73 and 83 positioned on the back side and judging whether the ratio of the two sums is greater than K, it is possible to discriminate between a foreign substance and a circuit pattern or to discriminate whether the foreign substance is one adhering to the laser light incidence side.

Also, since there is a correlation between the size of a foreign substance and the magnitude of a scatter signal, it is possible to know the size of the foreign substance from the peak value of the photoelectric signal or the like when the foreign substance has been detected. The signal whose peak value is to be obtained may be either the sum of the outputs of plural ones of the light-receiving elements on the laser light irradiation side or the signal from a predetermined light-receiving element.

If the moved position of the object to be inspected and the laser spot scanning position when a foreign substance has been detected are found, it is possible to know the position of the foreign substance lying on the object to be inspected.

As described above, according to the present invention, scattered lights are photoelectrically detected on the front and back sides of the object to be inspected and foreign substance inspection is carried out on the basis of the difference between the photoelectric signals, and this leads to the possibility of selectively accurately detecting whether the foreign substance adheres to the front side or the back side of the object to be inspected.

Also, when particularly a photomask or a reticle for the manufacture of IC is to be inspected, a plurality of light-receiving elements are disposed in different directions and the light beam is made to be obliquely incident and therefore, foreign substances alone can be rapidly detected, with the influence of the circuit pattern being prevented. Further, from the correlation between the intensity of the scattered light and the size of a foreign substance, the size of the foreign substance can be detected and only foreign substances of truly detrimental size can be detected. This can prevent the time loss which would otherwise result from detecting even unnecessarily small foreign substances to thereby re-clean a reticle or a mask usable for exposure with such reticle or mask being judged as a contaminated one.

The present invention can be utilized not only for the detection of foreign substances adhering to a reticle or a mask but also for the detection of foreign substances on an object comprising a transparent body having a pattern in intimate contact therewith, and therefore the present invention is very useful for inspection during the manufacture of precision patterns which dislike adherence of foreign substances such as dust or the like.

We claim:

1. An apparatus for detecting the presence of a foreign substance adhering to a planar substrate having a light-transmitting property, comprising:
   (a) irradiating means capable of emitting a light beam incident on one surface of said substrate obliquely relative to said surface;
   (b) means for displacing said irradiating means and said substrate relative to each other so that the position of incidence of said light beam onto said substrate is scanned on said one surface;
   (c) metering means capable of receiving a plurality of irregular reflected light beams irregularly reflected toward different directions by the foreign substance on said surface and producing a plurality of electrical outputs corresponding to the intensities of light of said plurality of irregular reflected light beams, said metering means including first light-receiving means disposed in opposed relationship with said one surface of said substrate and second light-receiving means disposed in opposed relationship with the other surface of said substrate; and
   (d) means for deciding the presence of said foreign substance on the basis of said plurality of electrical outputs.

2. An apparatus according to claim 1, wherein said first light-receiving means is disposed outside the optical path of the regular reflected light beam of said light beam regularly reflected on said one surface, and said second light-receiving means is disposed outside the optical path of said light beam directly passed through said substrate.

3. An apparatus according to claim 2, wherein said first and second light-receiving means are disposed in substantially plane-symmetric relation with respect to the plane of said substrate.

4. An apparatus according to claim 3, wherein said first light-receiving means includes photoelectric converting means having a light-receiving surface opposed to the position of incidence of said light beam onto said substrate.

5. An apparatus according to claim 4, wherein said light-receiving surface is provided so as to look to said incidence position obliquely with respect to the plane of said substrate.

6. An apparatus according to claim 3, wherein said metering means further includes third light-receiving means disposed in opposed relationship with said one surface of said substrate and fourth light-receiving means disposed in opposed relationship with the other surface of said substrate, said third and fourth light-receiving means being disposed in substantially plane-symmetric relationship with respect to the plane of said substrate.

7. An apparatus according to claim 6, wherein said metering means further includes fifth light-receiving means disposed in opposed relationship with said one surface of said substrate, said fifth light-receiving means being disposed at a position substantially opposed to said first light-receiving means with respect to the incidence position of said light beam.

8. An apparatus according to claim 7, wherein said metering means further includes sixth light-receiving means disposed in substantially plane-symmetric relationship with said fifth light-receiving means with respect to the plane of said substrate.

9. An apparatus according to claim 1, wherein said deciding means includes means for comparing said plurality of electrical outputs with each other.

10. An apparatus for detecting the presence of a foreign substance adhering to a planar substrate having a light-transmitting property, comprising:
    (a) irradiating means capable of emitting a light beam incident on one surface of said substrate obliquely relative to said surface;
    (b) first metering means including a plurality of light-receiving means disposed so as to look to the incidence position of said light beam on one surface side of said substrate from different directions and to be capable of receiving an irregular reflected light emitted to said one surface side, each of said light-receiving means producing an electrical output corresponding to the intensity of light received thereby;
    (c) second metering means disposed in substantially plane-symmetric relationship with said first metering means with respect to said substrate and including a plurality of light-receiving means capable of receiving an irregular reflected light emitted to the other surface side of said substrate, each of said light-receiving means producing an electrical output corresponding to the intensity of light received thereby;
    (d) means for detecting the light-receiving means having detected a minimum intensity of light from the electrical outputs of said first metering means; and
    (e) means for comparing the electrical output of said detected light-receiving means with the electrical output of at least one of said light-receiving means of said second metering means.

11. An apparatus according to claim 10, wherein said first metering means includes first and second light-receiving means, and said second metering means includes third and fourth light-receiving means, each of which is disposed in substantially plane-symmetric relationship with each of said first and second light-receiving means with respect to the plane of said substrate.

12. An apparatus according to claim 11, wherein said comparing means compares electrical output of said detected light-receiving means with electrical output of one of said third and fourth light-receiving means, one of them being in said plane-symmetric relationship with said detected light-receiving means.

13. An apparatus for detecting the presence of a foreign substance adhering to a planar substrate, comprising:
    (a) irradiating means capable of emitting a light beam incident on one surface of said substrate obliquely relative to said surface;
    (b) means for displacing said irradiating means and said substrate relative to each other so that the position of incidence of said light beam onto said substrate is scanned on said one surface;
    (c) metering means receiving a plurality of irregular reflected light beams of said light beam which have been irregularly reflected on said surface toward different directions and producing a plurality of electrical outputs corresponding to the intensities of light of said plurality of irregular reflected light beams, said metering means including a plurality of light-receiving means disposed fixedly with said substrate;
    (d) means for generating a positional output which is responsive to said displacing means and which corresponds to said position of incidence of said light beam;

(e) a plurality of amplifying means for independently amplifying each of said plurality of electrical outputs, each of amplifying means having an amplification degree which changes in response to said positional output; and (f) means for deciding the presence of said foreign substance on the basis of said plurality of electrical outputs amplified by said plurality of amplifying means, respectively.

14. An apparatus according to claim 13, wherein said metering means includes first and second light-receiving means disposed outside the optical path of the regular reflected light beam of said light beam regularly reflected on said surface, each of said first and second light-receiving means being disposed at a position substantially opposed with respect to the incidence position of said light beam.

15. An apparatus according to claim 14, wherein said metering means further includes third light-receiving means provided in substantially opposed relationship with said second light-receiving means near said first light-receiving means outside the optical path of said regular reflected light beam.

16. An apparatus according to claim 13, wherein said deciding means includes means for producing a reference output and means for comparing each of said electrical outputs with said reference output.

17. An apparatus for detecting the presence of a foreign substance adhering to a planar substrate having a light-transmitting property, comprising:

(a) irradiating means capable of emitting a light beam incident on one surface of said substrate obliquely relative to said surface;

(b) means for displacing said irradiating means and said substrate relative to each other so that the position of incidence of said light beam onto said substrate is scanned on said one surface;

(c) metering means capable of receiving a plurality of irregular reflected light beams irregularly reflected toward different directions by the foreign substance on said surface and producing a plurality of electrical outputs corresponding to the intensities of light of said plurality of irregular reflected light beams, said metering means including at least first and second light-receiving means disposed in opposed relationship with said substrate;

(d) means for generating a slice level output which is responsive to said displacing means and which changes according to said position of incidence of said light beam; and (e) means for deciding the presence of said foreign substance on the basis of said plurality of electrical outputs, said deciding means including first comparing means which compares the electric output of said first light-receiving means with said slice level output, and second comparing means which compares the electric outputs of said first and second light-receiving means with each other.

18. An apparatus according to claim 17, wherein said first light-receiving means is disposed in opposed relationship with said one surface of said substrate and said second light-receiving means is disposed in opposed relationship with the other surface of said substrate.

* * * * *